(12) United States Patent
Tierney et al.

(10) Patent No.: US 7,524,320 B2
(45) Date of Patent: *Apr. 28, 2009

(54) MECHANICAL ACTUATOR INTERFACE SYSTEM FOR ROBOTIC SURGICAL TOOLS

(75) Inventors: Michael J. Tierney, Pleasanton, CA (US); Thomas G. Cooper, Menlo Park, CA (US); Chris A. Julian, Los Gatos, CA (US); Stephen J. Blumenkranz, Redwood City, CA (US); Gary S. Guthart, Foster City, CA (US); Robert G. Younge, Portola Valley, CA (US)

(73) Assignee: Intuitive Surgical, Inc., Sunnyvale, CA (US)

( * ) Notice: Subject to any disclaimer, the term of this patent is extended or adjusted under 35 U.S.C. 154(b) by 1036 days.

This patent is subject to a terminal disclaimer.

(21) Appl. No.: 10/316,666

(22) Filed: Dec. 10, 2002

(65) Prior Publication Data

US 2003/0083673 A1 May 1, 2003

Related U.S. Application Data

(60) Continuation of application No. 09/929,453, filed on Aug. 13, 2001, now Pat. No. 7,048,745, which is a division of application No. 09/418,726, filed on Oct. 15, 1999, now Pat. No. 6,331,181.

(60) Provisional application No. 60/111,713, filed on Dec. 8, 1998.

(51) Int. Cl.
*A61B 19/00* (2006.01)

(52) U.S. Cl. .......................................... 606/130; 606/1

(58) Field of Classification Search ...................... 606/1, 606/130; 700/259, 260, 263
See application file for complete search history.

(56) References Cited

U.S. PATENT DOCUMENTS 4,038,987 A 8/1977 Komiya (Continued)

FOREIGN PATENT DOCUMENTS

JP 7-194610 8/1995

(Continued)

OTHER PUBLICATIONS

Alexander, Arthur D., III., "Impacts of Telemanipulation on Modern Society," *International Centre for Mechanical Sciences*, Courses and Lectures No. 201, vol. II, pp. 122-136 (Sep. 5-8, 1973).

(Continued)

*Primary Examiner*—Eduardo C Robert
*Assistant Examiner*—James L Swiger, III

(57) ABSTRACT

Robotic surgical tools, systems, and methods for preparing for and performing robotic surgery include a memory mounted on the tool. The memory can perform a number of functions when the tool is loaded on the tool manipulator: first, the memory can provide a signal verifying that the tool is compatible with that particular robotic system. Secondly, the tool memory may identify the tool-type to the robotic system so that the robotic system can reconfigure its programming. Thirdly, the memory of the tool may indicate tool-specific information, including measured calibration offsets indicating misalignment of the tool drive system, tool life data, or the like. This information may be stored in a read only memory (ROM), or in a nonvolatile memory which can be written to only a single time. The invention further provides improved engagement structures for coupling robotic surgical tools with manipulator structures.

31 Claims, 22 Drawing Sheets

U.S. PATENT DOCUMENTS

| | | | |
|---|---|---|---|
| 4,149,278 | A | 4/1979 | Wiker et al. |
| 4,281,447 | A | 8/1981 | Miller et al. |
| 4,332,066 | A | 6/1982 | Hailey et al. |
| 4,367,998 | A | 1/1983 | Causer |
| 4,386,933 | A | 6/1983 | Sanchez |
| 4,456,960 | A | 6/1984 | Wakai |
| 4,486,928 | A | 12/1984 | Tucker et al. |
| 4,500,065 | A | 2/1985 | Hennekes et al. |
| 4,511,305 | A | 4/1985 | Kawai et al. |
| 4,512,709 | A | 4/1985 | Hennekes et al. |
| 4,706,372 | A | 11/1987 | Ferrero et al. |
| 4,710,093 | A | 12/1987 | Zimmer et al. |
| 4,744,363 | A | 5/1988 | Hasson |
| 4,751,925 | A | 6/1988 | Tontarra |
| 4,766,775 | A | 8/1988 | Hodge |
| 4,793,053 | A | 12/1988 | Zuccaro et al. |
| 4,809,747 | A | 3/1989 | Choly et al. |
| 4,830,569 | A | 5/1989 | Jannborg |
| 4,832,198 | A | 5/1989 | Alikhan |
| 4,837,703 | A | 6/1989 | Kakazu et al. |
| 4,928,546 | A | 5/1990 | Walters |
| 4,943,939 | A | 7/1990 | Hoover |
| 4,979,949 | A | 12/1990 | Matsen, III et al. |
| 4,996,975 | A | 3/1991 | Nakamura |
| 5,018,266 | A | 5/1991 | Hutchinson et al. |
| 5,078,140 | A | 1/1992 | Kwoh |
| 5,086,401 | A * | 2/1992 | Glassman et al. ............ 700/259 |
| 5,143,453 | A | 9/1992 | Weynant née Girones |
| 5,154,717 | A | 10/1992 | Matsen, III et al. |
| 5,155,693 | A | 10/1992 | Altmayer et al. |
| 5,174,300 | A | 12/1992 | Bales et al. |
| 5,184,601 | A | 2/1993 | Putman |
| 5,217,003 | A | 6/1993 | Wilk |
| 5,221,283 | A | 6/1993 | Chang |
| 5,236,432 | A | 8/1993 | Matsen, III et al. |
| 5,243,266 | A * | 9/1993 | Kasagami et al. ......... 318/568.1 |
| 5,255,429 | A | 10/1993 | Nishi et al. |
| 5,257,998 | A | 11/1993 | Ota et al. |
| 5,271,384 | A | 12/1993 | McEwen et al. |
| 5,294,209 | A | 3/1994 | Naka et al. |
| 5,305,203 | A | 4/1994 | Raab |
| 5,312,212 | A | 5/1994 | Naumec |
| 5,313,935 | A | 5/1994 | Kortenbach et al. |
| 5,337,732 | A | 8/1994 | Grundfest et al. |
| 5,339,799 | A * | 8/1994 | Kami et al. ................. 600/117 |
| 5,343,385 | A | 8/1994 | Joskowicz et al. |
| 5,354,314 | A | 10/1994 | Hardy et al. |
| 5,355,743 | A | 10/1994 | Tesar |
| 5,359,993 | A | 11/1994 | Slater et al. |
| 5,372,147 | A | 12/1994 | Lathrop, Jr. et al. |
| 5,397,323 | A | 3/1995 | Taylor |
| 5,399,951 | A | 3/1995 | Lavallee et al. |
| 5,400,267 | A | 3/1995 | Denen et al. |
| 5,402,801 | A | 4/1995 | Taylor |
| 5,403,319 | A | 4/1995 | Matsen, III et al. |
| 5,417,210 | A | 5/1995 | Funda et al. |
| 5,427,097 | A | 6/1995 | Depp |
| 5,451,368 | A | 9/1995 | Jacob |
| 5,520,678 | A | 5/1996 | Heckele et al. |
| 5,617,857 | A | 4/1997 | Chader et al. |
| 5,624,398 | A | 4/1997 | Smith et al. |
| 5,630,431 | A * | 5/1997 | Taylor ....................... 128/897 |
| 5,631,973 | A | 5/1997 | Green |
| 5,649,956 | A | 7/1997 | Jensen et al. |
| 5,690,635 | A | 11/1997 | Baumgarten et al. |
| 5,695,500 | A | 12/1997 | Taylor et al. |
| 5,695,501 | A | 12/1997 | Carol et al. |
| 5,697,939 | A | 12/1997 | Kubota et al. |
| 5,710,870 | A * | 1/1998 | Ohm et al. .................. 700/263 |
| 5,762,458 | A | 6/1998 | Wang et al. |
| 5,784,542 | A * | 7/1998 | Ohm et al. .................. 700/260 |
| 5,792,135 | A | 8/1998 | Madhani et al. |
| 5,797,900 | A | 8/1998 | Madhani et al. |
| 5,800,423 | A | 9/1998 | Jensen |
| 5,807,377 | A | 9/1998 | Madhani et al. |
| 5,808,665 | A | 9/1998 | Green |
| 5,814,038 | A | 9/1998 | Jensen et al. |
| 5,817,084 | A | 10/1998 | Jensen |
| 5,855,583 | A | 1/1999 | Wang et al. |
| 5,876,325 | A | 3/1999 | Mizuno et al. |
| 5,878,193 | A | 3/1999 | Wang et al. |
| 5,976,122 | A | 11/1999 | Madhani et al. |
| 6,132,368 | A | 10/2000 | Cooper |
| 6,151,981 | A | 11/2000 | Costa |
| 6,246,200 | B1 | 6/2001 | Blumenkranz et al. |
| 6,259,806 | B1 * | 7/2001 | Green ........................ 382/128 |
| 6,331,181 | B1 | 12/2001 | Tierney et al. |
| 6,346,072 | B1 | 2/2002 | Cooper |
| 6,370,411 | B1 | 4/2002 | Osadchy et al. |
| 6,398,726 | B1 * | 6/2002 | Ramans et al. .............. 600/229 |
| 6,424,885 | B1 | 7/2002 | Niemeyer et al. |
| 6,434,507 | B1 | 8/2002 | Clayton et al. |
| 6,468,265 | B1 * | 10/2002 | Evans et al. ..................... 606/1 |
| 6,491,701 | B2 | 12/2002 | Tierney et al. |
| 6,554,844 | B2 * | 4/2003 | Lee et al. ..................... 606/130 |
| 6,699,177 | B1 | 3/2004 | Wang et al. |
| 6,738,656 | B1 | 5/2004 | Ferre et al. |
| 6,866,671 | B2 | 3/2005 | Tierney et al. |
| 2002/0032452 | A1 | 3/2002 | Tierney et al. |

FOREIGN PATENT DOCUMENTS

| | | |
|---|---|---|
| WO | WO 93/13916 | 7/1993 |
| WO | WO 94/26167 | 11/1994 |
| WO | WO 95/16396 | 6/1995 |
| WO | WO 95/30964 | 11/1995 |
| WO | WO 96/39944 | 12/1996 |
| WO | WO 97/29710 | 8/1997 |
| WO | WO 98/25666 | 6/1998 |
| WO | WO 99/50721 | 10/1999 |
| WO | WO 00/33755 | 6/2000 |

OTHER PUBLICATIONS

Madhani et al., "The black falcon: A teleoperated surgical instrument for minimally invasive surgery" (submitted to IROS 1998) 9 pages total.

Moyer, T.H., Thesis entitled "The design of an integrated hand and wrist mechanism" for Master of Science in Mechanical Engineering at the Massachusetts Institute of Technology (1992) pp. 1-106.

Neisius et al., "Robotic manipulator for endoscopic handling of surgical effectors and cameras" Proceedings of the First International Symposium on Medical Robotics and Computer Assisted Surgery, vol. 2, Workshop (Part I & II)- Session VI, pp. 169-175.

Salisbury, J.K., "Kinematic and force analysis of articulated hands" Department of Computer Science, Stanford University, Report No. STAN-CS-82-921 (1982) Chapter 9, pp. 67-77.

Thring, "Robots and telechirs: Manipulators with memory; remote manipulators; machine limbs for the handicapped" (1993) M.W. Thring/Ellis Horwood Ltd. pp. 9-11, 122-131, 194-195, 235-257, 274-279.

"Task 2: Miniature end effector—A preliminary design" pp. 32-47.

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

* cited by examiner

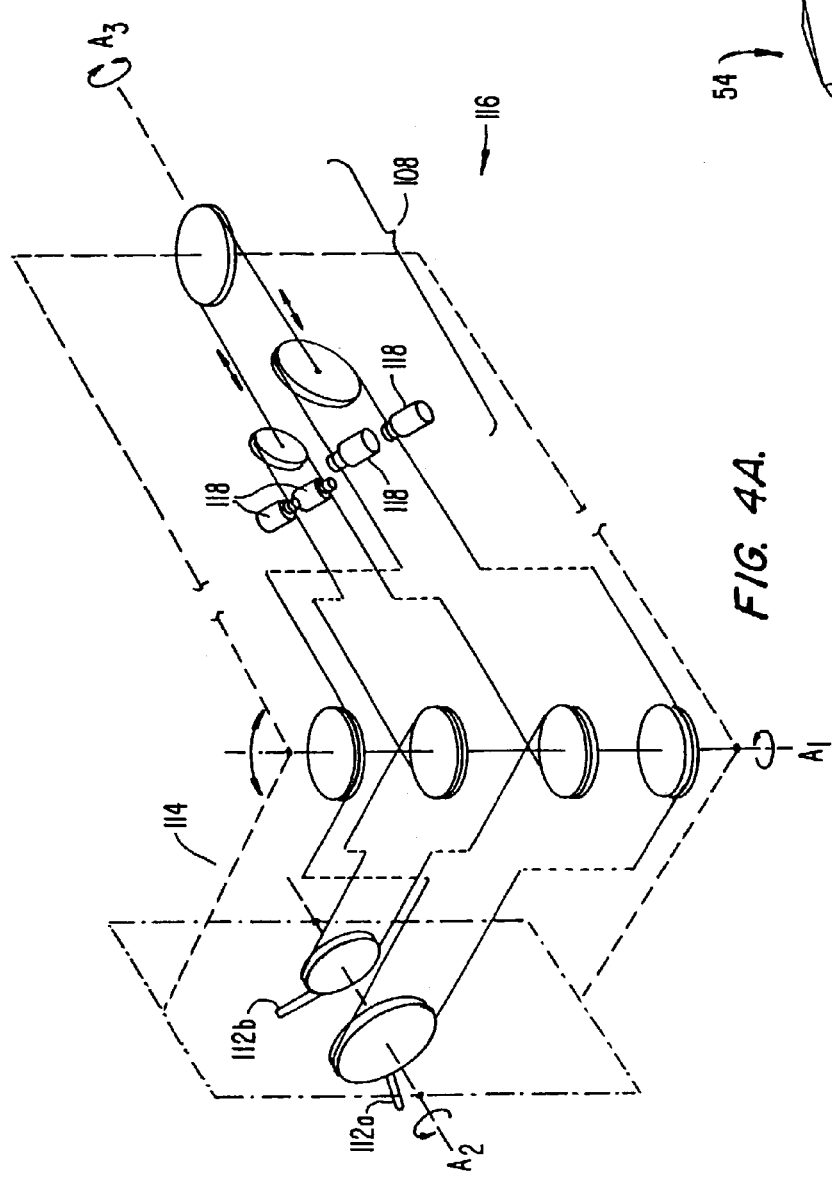
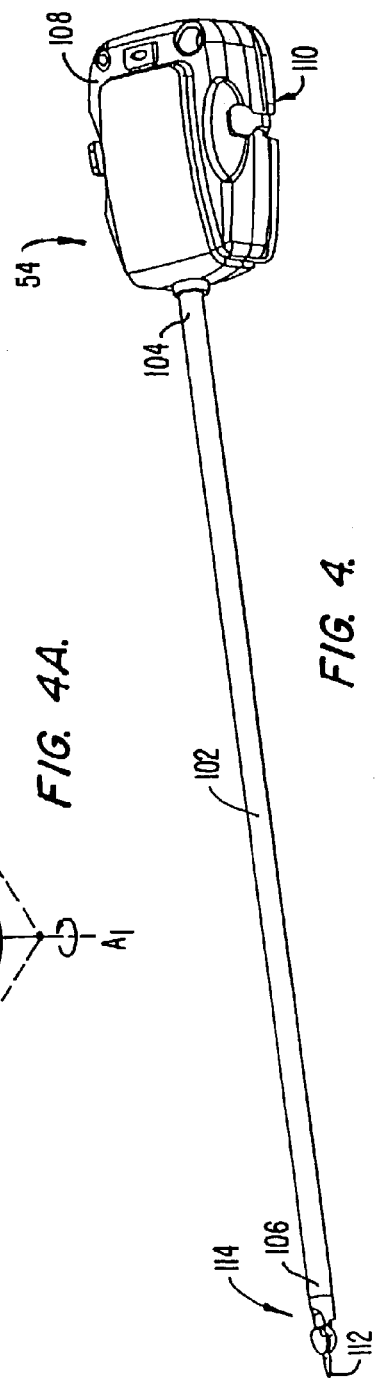

MECHANICAL ACTUATOR INTERFACE SYSTEM FOR ROBOTIC SURGICAL TOOLS

CROSS-REFERENCES TO RELATED APPLICATIONS

The present application is a continuation of U.S. patent application Ser. No. 09/929,453 filed on Aug. 13, 2001, and is a divisional application of U.S. patent application Ser. No. 09/759,542 filed Jan. 12, 2001, now U.S. Pat. No. 6,491,701, which is a continuation application of U.S. patent application Ser. No. 09/418,726 filed Dec. 6, 1999, and in turn also claims priority to U.S. Provisional Patent Application No. 60/111,713 filed on Dec. 8, 1998; U.S. patent application Ser. No. 09/398,958 filed Sep. 17, 1999, now U.S. Pat. No. 6,394,998; and U.S. Provisional Patent Application No. 60/116,844 filed on Jan. 2, 1999, entitled "Surgical Tools For Use In Minimally Invasive Telesurgical Applications". The entirety of the above-referenced applications is herein incorporated by reference.

This application also incorporates by references the following U.S. Design patent application Ser. Nos. 29/097,544 filed on Dec. 8, 1998, entitled "Portion Of An Interface For A Medical Instrument"; 29/097,552 filed on Dec. 8, 1998, entitled "Interface For A Medical Instrument"; 29/097,550 filed on Dec. 8, 1998, entitled "Portion Of An Adaptor For A Medical Instrument"; and 29/097,551 filed on Dec. 8, 1998, entitled "Adaptor For A Medical Instrument".

BACKGROUND OF THE INVENTION

This invention relates to robotically assisted surgery, and more particularly provides surgical tools having improved mechanical and/or data interface capabilities to enhance the safety, accuracy, and speed of minimally invasive and other robotically enhanced surgical procedures.

In robotically assisted surgery, the surgeon typically operates a master controller to remotely control the motion of surgical instruments at the surgical site. The controller may be separated from the patient by a significant distance (e.g., across the operating room, in a different room, or in a completely different building than the patient). Alternatively, a controller may be positioned quite near the patient in the operating room. Regardless, the controller will typically include one or more hand input devices (such as joysticks, exoskeletol gloves, master manipulators, or the like) which are coupled by a servo mechanism to the surgical instrument. More specifically, servo motors move a manipulator or "slave" supporting the surgical instrument based on the surgeon's manipulation of the hand input devices. During an operation, the surgeon may employ, via the robotic surgery system, a variety of surgical instruments such as tissue graspers, needle drivers, electrosurgical cautery probes, etc. Each of these structures performs functions for the surgeon, for example, holding or driving a needle, grasping a blood vessel, or dissecting, cauterizing, or coagulating tissue.

This new method of performing robotic surgery has, of course, created many new challenges. One such challenge is that a surgeon will typically employ a significant number of different surgical instruments during each surgical procedure. The number of independent surgical manipulators will often be limited due to space constraints and cost. Additionally, patient trauma can generally be reduced by eliminating the number of tools used at any given time. More specifically, in minimally invasive procedures, the number of entry ports into a patient is generally limited because of space constraints, as well as a desire to avoid unnecessary incisions in the patient. Hence, a number of different surgical instruments will typically be introduced through the same trocar sleeve into the abdomen during, for example, laparoscopic procedures. Likewise, in open surgery, there is typically not enough room adjacent the surgical site to position more than a few surgical manipulators, particularly where each manipulator/tool combination has a relatively large range of motion. As a result, a number of surgical instruments will often be attached and detached from a single instrument holder of a manipulator during an operation.

Published PCT application WO98/25666, filed on Dec. 10, 1997 and assigned to the present assignee (the full disclosure of which is incorporated herein by reference) describes a Multicomponent Telepresence System and Method which significantly improves the safety and speed with which robotic surgical tools can be removed and replaced during a surgical procedure. While this represents a significant advancement of the art, as is often true, still further improvements would be desirable. In particular, each tool change which occurs during a surgical procedure increases the overall surgery time. While still further improvements in the mechanical tool/manipulator interface may help reduce a portion of this tool change time, work in connection with the present invention has shown that the mechanical removal and replacement of the tool may represent only one portion of the total interruption for a tool change. U.S. Pat. No. 5,400,267 describes a memory feature for electrically powered medical equipment, and is also incorporated herein by reference.

As more and more different surgical tools are provided for use with a robotic system, the differences between the tool structures (and the interaction between the tool and the other components of the robotic system) become more pronounced. Many of these surgical tools will have one or more degrees of motion between the surgical end effectors and the proximal interface which engages the tool to the holder of the manipulator. The desired and/or practicable ranges of motion for an electrosurgical scalpel may be significantly different than those of a clip applier, for example. Work in connection with the present invention has found that even after a tool is properly placed on the surgical manipulator, the time involved in reconfiguring the robotic system to take advantage of a different tool, and to perfect the master controller's effective control over the degrees of motion of the tool, may add significantly to the total tool change delay.

In light of the above, it would be desirable to provide improved robotic surgery tools, systems, and method. It would further be desirable to provide techniques for reducing the total delay associated with each tool change. It would be especially desirable if these enhanced, and often more rapid, robotic tool change techniques resulted in still further improvement in the safety and reliability of these promising surgical systems.

BRIEF SUMMARY OF THE INVENTION

The present invention generally provides improved robotic surgical devices, systems, and methods for preparing for and performing robotic surgery. The robotic tools of the present invention will often make use of a memory structure mounted on a tool, manipulator arm, or movable support structure. The memory can, for example, perform a number of important functions when a tool is loaded on the tool manipulator: first, the memory can provide a signal verifying that the tool is compatible with that particular robotic system. Secondly, the tool memory may identify the tool-type (whether it is a scalpel, needle grasper, jaws, scissors, clip applier, electrocautery blade, or the like) to the robotic system so that the robotic system can reconfigure its programming to take full advantage of the tools' specialized capabilities. This tool-type data may simply be an identification signal referencing further data in a look-up table of the robotic system. Alternatively, the tool-type signal provided by the tool may define the tool characteristics in sufficient detail to allow reconfiguration of the robotic programming without having to resort to an external table. Thirdly, the memory of the tool may indicate tool-specific information, including (for example) measured calibration offsets indicating misalignment between the tool drive system and the tool end effector elements, tool life data (such as the number of times the tool has been loaded onto a surgical system, the number of surgical procedures performed with the tool, and/or the total time the tools has been used), or the like. The information may be stored in some form of non-volatile memory such as one-time programmable EPROM, Flash EPROM, EEPROM, battery-backed-up SRAM, or similar memory technology where data can be updated and retained in either a serial or random access method, or with any of a wide variety of alternative hardware, firmware, or software. The invention further provides improved engagement structures for coupling robotic surgical tools with manipulator structures.

In a first aspect, the invention provides a robotic surgical tool for use in a robotic surgical system. The robotic surgical system has a processor which directs movement of a tool holder. The tool comprises a probe having a proximal end and a distal end. A surgical end effector is disposed adjacent the distal end of the probe. An interface is disposed adjacent to the proximal end of the probe. The interface can be releasably coupled with the tool holder. Circuitry is mounted on the probe. The circuitry defines a signal for transmitting to the processor so as to indicate compatibility of the tool with the system.

The tool will often comprise a surgical instrument suitable for manipulating tissue, an endoscope or other image capture device, or the like. Preferably, the signal will comprise unique tool identifier data. The processor of the robotic surgical system may include programming to manipulate the tool identifier according to a pre-determined function or algorithm so as to derive verification data. The signal transmitted to the processor will often include the verification data. Alternative compatibility signals may include a signal which is listed in a table accessible to the processor, an arbitrary compatibility data string, or the like.

In another aspect, the invention provides a robotic surgical component for use in a robotic surgical system having a processor and a component holder. The component comprises a component body having an interface mountable to the component holder. The body supports a surgical end effector, and a drive system is coupled to the body for moving the end effector per commands from the processor. Circuitry is mounted on the body and defines a signal for transmitting to the processor. The signal may indicate compatibility of the component with the system, may define a component type of the component, may indicate coupling of the component to the system, and/or may indicate calibration of the component. Typically, the component will comprise a surgical tool, a manipulator arm, a pre-positioning linkage supporting the manipulator arm, or the like.

In another aspect, the invention provides a method for installing a robotic surgical component in a robotic surgical system. The method comprises mounting the component to a component holder. A signal is transmitted from the component to a processor of the robotic surgical system. The component is articulated in response to the signal per commands of the processor.

In many embodiments, compatibility of the component with the robotic surgical system will be verified using the signal transmitted from the component to the processor. This can be accomplished by providing unique identification data on the component, and deriving verification data from the identification data according to an algorithm. The verification data is stored with a memory of the component, the signal transmitted to the processor including both the identification and verification data. The algorithm may then be performed on the transmitted unique identification data with the processor, and the results compared with the verification data. Advantageously, this method can take advantage of unique identification data which is often unalterably stored in a memory of commercially available integrated circuits.

In another aspect, the invention provides a robotic surgical tool for use in robotic surgical systems having a processor. The tool comprises a shaft having a proximal end and a distal end. A surgical end effector is disposed adjacent the distal end of the shaft. The end effector has a plurality of degrees of motion relative to the proximal end. An interface is disposed adjacent the proximal end of the shaft. The interface can be releasably coupled with a robotic probe holder. The interface comprises a plurality of driven elements. A plurality of tool drive systems couple the driven elements to the degrees of motion of the end effector. The tool drive system has calibration offsets between a nominal relative position of the end effector and the driven elements, and a measured relative position of the end effector and driven elements. A memory stores data indicating the offsets. The memory is coupled to the interface so as to transmit the offsets to the processor.

In yet another aspect, the invention provides a robotic surgical system comprising a plurality of tools of different tool-types. Each tool comprises an elongate shaft with a cross-section suitable for introduction into an internal surgical site within a patient body via a minimally invasive opening. A distal surgical end effector is coupled to the shaft by at least one joint. The joint is drivingly coupled to a proximal interface by a tool drive system. Circuitry of the tool transmits a tool-type via the interface. The tool types may optionally differ in at least one characteristic such as joint geometry, end effector geometry, drive system characteristics, end effector or drive system strength, or the like. The system also includes a robotic manipulator including a linkage supporting a tool holder. The tool holder releasably receives the interface. A manipulator drive motor drivingly engages the linkage so as to move the tool holder relative to the opening and position the shaft within the surgical site. A tool drive motor is coupled to the tool holder so as to drivingly engage the tool drive system and articulate the joint. A processor is coupled to the tool holder. The processor has programming that effects a desired movement of the end effector by transmitting drive signals to the tool drive motors of the manipulator. The processor reconfigures the program for the different joint geometries based on the tool-type signals.

In another aspect, the invention provides a robotic surgical system comprising a surgical tool having a surgical end effector and an interface. A manipulator assembly has a base and a tool holder for releasably engaging the interface. A plurality of tool engagement sensors are coupled to the tool holder. Each tool sensor produces a signal when the interface engages the holder. A processor is coupled to the tool engagement sensors. The processor has a tool change mode and a tissue manipulation mode. The processor requires tool signals from each of the sensors before changing the tool change mode to the tissue manipulation mode. The processor remains in the tissue manipulation mode when at least one, but not all, of the tool signals is lost.

The tools used in robotic surgery will be subjected to significant structural stress during use. The stress may result in temporary loss of an engagement signal from an engagement sensor. By providing at least two, and preferably three engagement sensors, the surgical procedure can continue safely with the loss of an engagement signal from an individual sensor so long as the system can still verify proper engagement between the manipulator and tool. This arrangement results in a robust tool engagement sensing system that avoids frequent delays during the surgical procedure as might occur from the loss of an individual signal.

In yet another aspect, the invention provides a robotic surgical system comprising a manipulator assembly having a base and tool holder which moves relative to the base. The tool holder has a plurality of drive elements. A sterile drape covers at least a portion of the manipulator. A sterile tool has a proximal interface and distal end effector. The distal end effector has a plurality of degrees of motion relative to the proximal interface. The degrees of motion are coupled to drive elements of the interface. An adapter is disposed adjacent the sterile drape between the holder and the interface. The adapter comprises a plurality of movable bodies. Each movable body has a first surface driven by the drive elements of the holder, and a second surface driving the driven elements of the tool.

In yet another aspect, the invention provides a robotic surgical tool for use with a robotic manipulator having a tool holder. The tool holder has magnetically actuatable circuitry. The tool comprises a probe having a proximal end and a distal end. A surgical end effector is disposed adjacent the distal end of the probe. An interface adjacent the proximal end of the probe is releasably coupleable with the holder. The interface comprises a magnet positioned so as to actuate the circuitry of the holder.

DETAILED DESCRIPTION OF THE INVENTION

The present invention provides robotic surgery systems, devices, and methods. Robotic surgery will generally involve the use of multiple robotic arms. One or more of the robotic arms will often support a surgical tool which may be articulated (such as jaws, scissors, graspers, needle holders, microdissectors, staple appliers, tackers, suction/irrigation tools, clip appliers, or the like) or non-articulated (such as cutting blades, cautery probes, irrigators, catheters, suction orifices, or the like). One or more of the robotic arms will often be used to support one or more surgical image capture devices such as an endoscope (which may be any of the variety of structures such as a laparoscope, an arthroscope, a hysteroscope, or the like), or optionally, some other imaging modality (such as ultrasound, fluoroscopy, magnetic resonance imaging, or the like). Typically, the robotic arms will support at least two surgical tools corresponding to the two hands of a surgeon and one optical image capture device.

The present invention will find application in a variety of surgical procedures. The most immediate applications will be to improve existing minimally invasive surgical procedures, such as coronary artery bypass grafting and mitral and aortic valve repair and/or replacement. The invention will also have applications for surgical procedures which are difficult to perform using existing minimally invasive techniques, such as Nissen Fundoplications. Additionally, it is anticipated that these surgical systems will find uses in entirely new surgeries that would be difficult and/or impossible to perform using traditionally open or known minimally invasive techniques. For example, by synchronizing the movements of the image capture device and/or surgical tools with a tissue undergoing physiological movement (such a beating heart), the moving tissue may be accurately manipulated and treated without halting the physiological movement. Additional potential applications include vascular surgery (such as for the repair of thoracic and abdominal aneurysms), general and digestive surgeries (such as cholecystectomy, inguinale hernia repair, colon resection, and the like), gynecology (for fertility procedures, hysterectomies, and the like), and a wide variety of alternative procedures.

Figure 1:
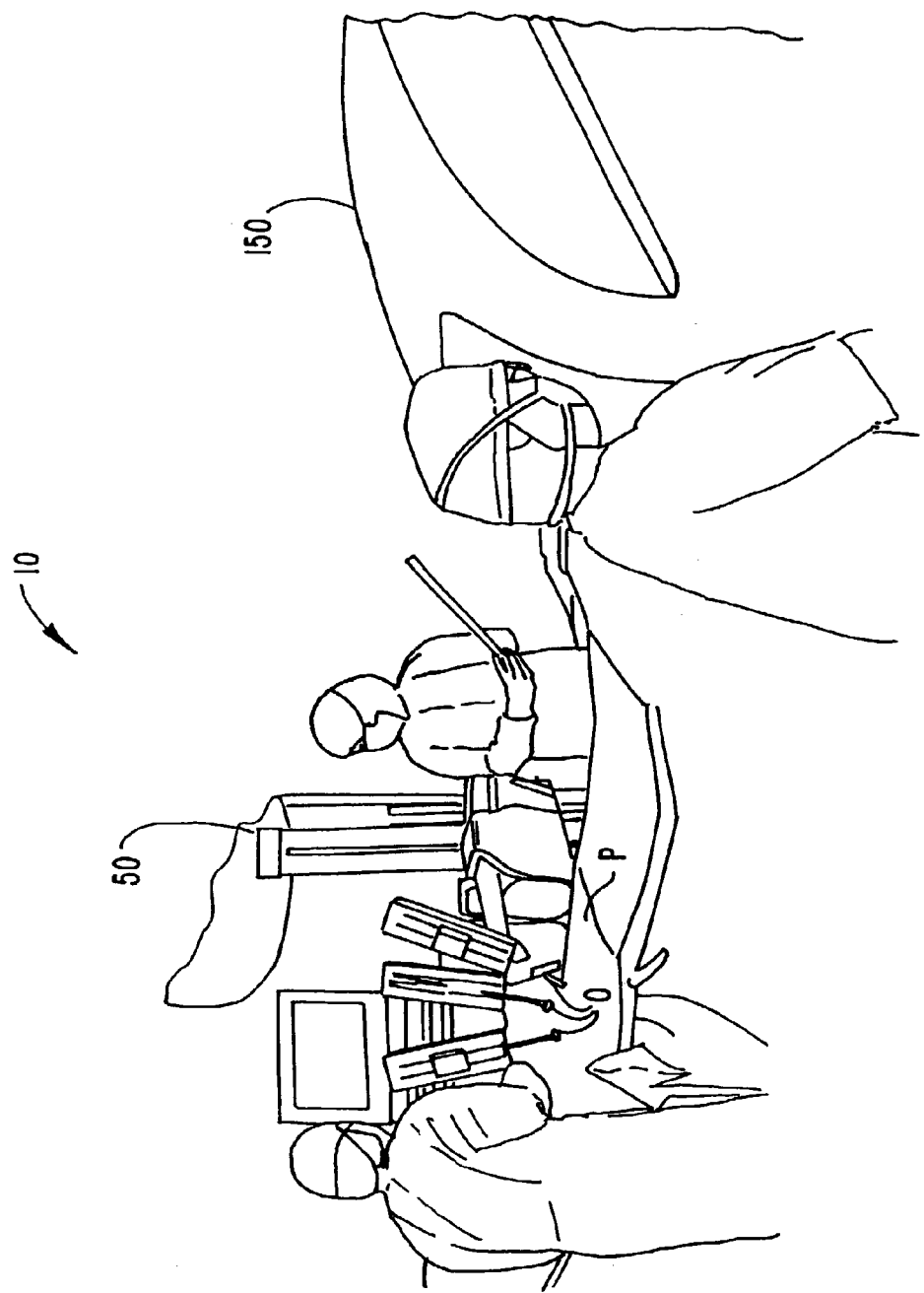
FIG. 1 illustrates a robotic surgical procedure in which a surgeon at a master station directs movement of robotic surgical tools effected by a slave manipulator, and shows an assistant preparing to change a tool mounted to a tool holder of the slave.

Referring now to FIG. 1, the robotic surgical system 10 generally includes master controller 150 and a robotic arm slave cart 50. Master controller 150 generally includes master controllers (not shown) which are grasped by the surgeon and manipulated in space while the surgeon views the procedure views a stereo display. The master controllers are manual input devices which preferably move with six degrees of freedom, and which often further have an actuatable handle for actuating tools (for example, for closing grasping saws, applying an electrical potential to an electrode, or the like). In this embodiment, the master control station 150 also includes a processor, as will be described in more detail hereinbelow.

Robotic arm cart 50 is positioned adjacent to patient body P and moves tools having shafts. The shafts extend into an internal surgical site within the patient body via openings O. As illustrated in FIG. 1, one or more assistant may be present during surgery to assist the surgeon, particularly during removal and replacement of tools. Robotic surgery systems and methods are further described in co-pending U.S. patent application Ser. No. 08/975,617, filed Nov. 21, 1997, the full disclosure of which is incorporated herein by reference.

Figure 2:
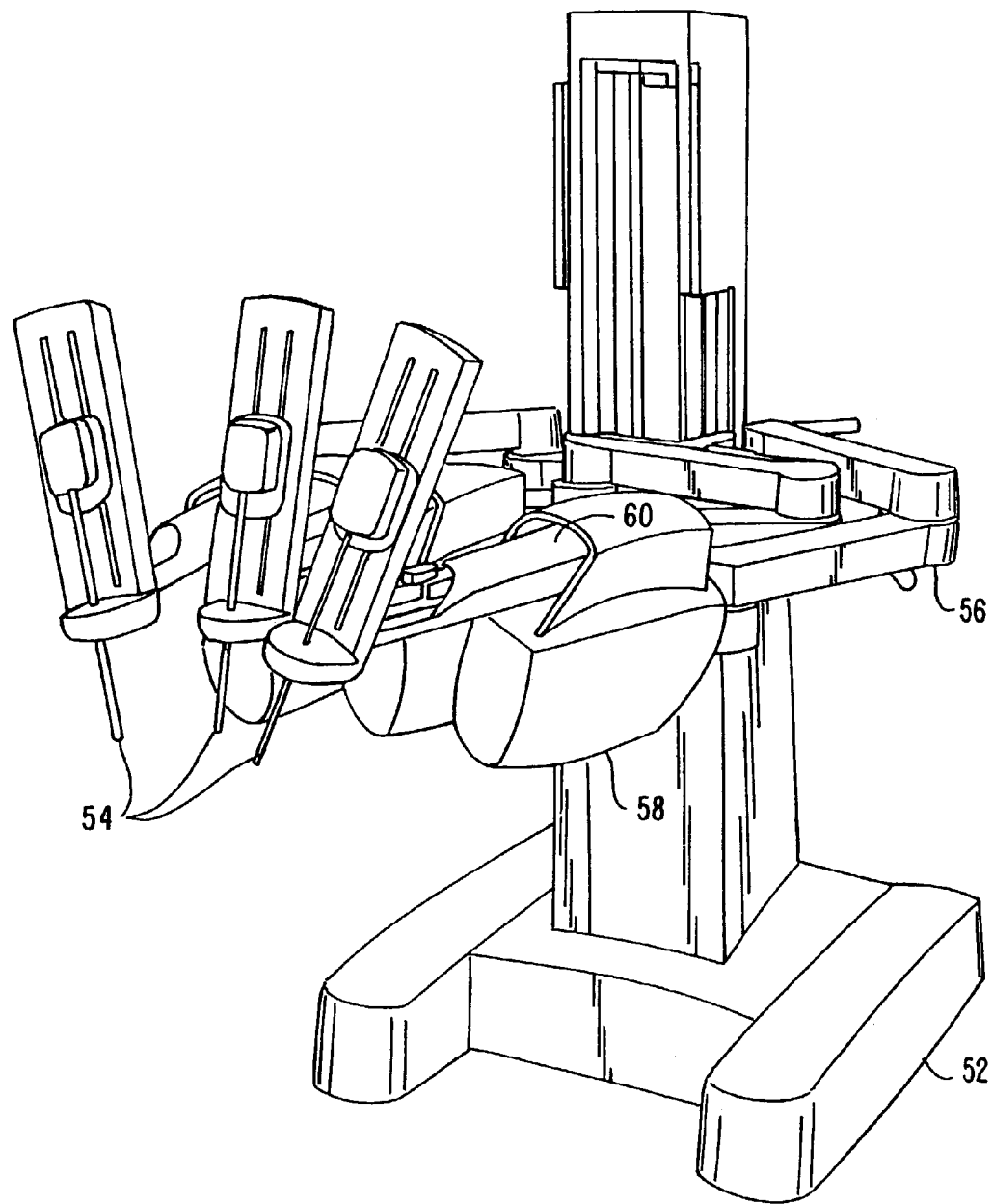
FIG. 2 is a perspective view of a robotic surgical arm cart system in which a series of passive set-up joints support robotically actuated manipulators (typically, the center arm would support a camera).

Robotic arm cart 50 is shown in isolation in FIG. 2. Cart 50 includes a base 52 from which three surgical tools 54 are supported. More specifically, tools 54 are each supported by a series of manually articulatable linkages, generally referred to as set-up joints 56, and a robotic manipulator 58. It should be noted that these structures are here illustrated with protective covers extending over much of the robotic linkage. It should be understood that these protective covers are optional, and may be limited in size or entirely eliminated in some embodiments to minimize the inertia that is manipulated by the servo mechanism, to limit the volume of moving components so as to avoid collisions, and to limit the overall weight of cart 50.

Cart 50 will generally have dimensions suitable for transporting the cart between operating rooms. The cart will typically fit through standard operating room doors and onto standard hospital elevators. The cart should have a weight and wheel (or other transportation) system that allows the cart to be positioned adjacent an operating table by a single attendant. The cart should have sufficient stability in the transport configuration to avoid tipping at minor discontinuities of the floor, and to easily withstand overturning moments that will be imposed at the ends of the robotic arms during use.

Figure 2A:
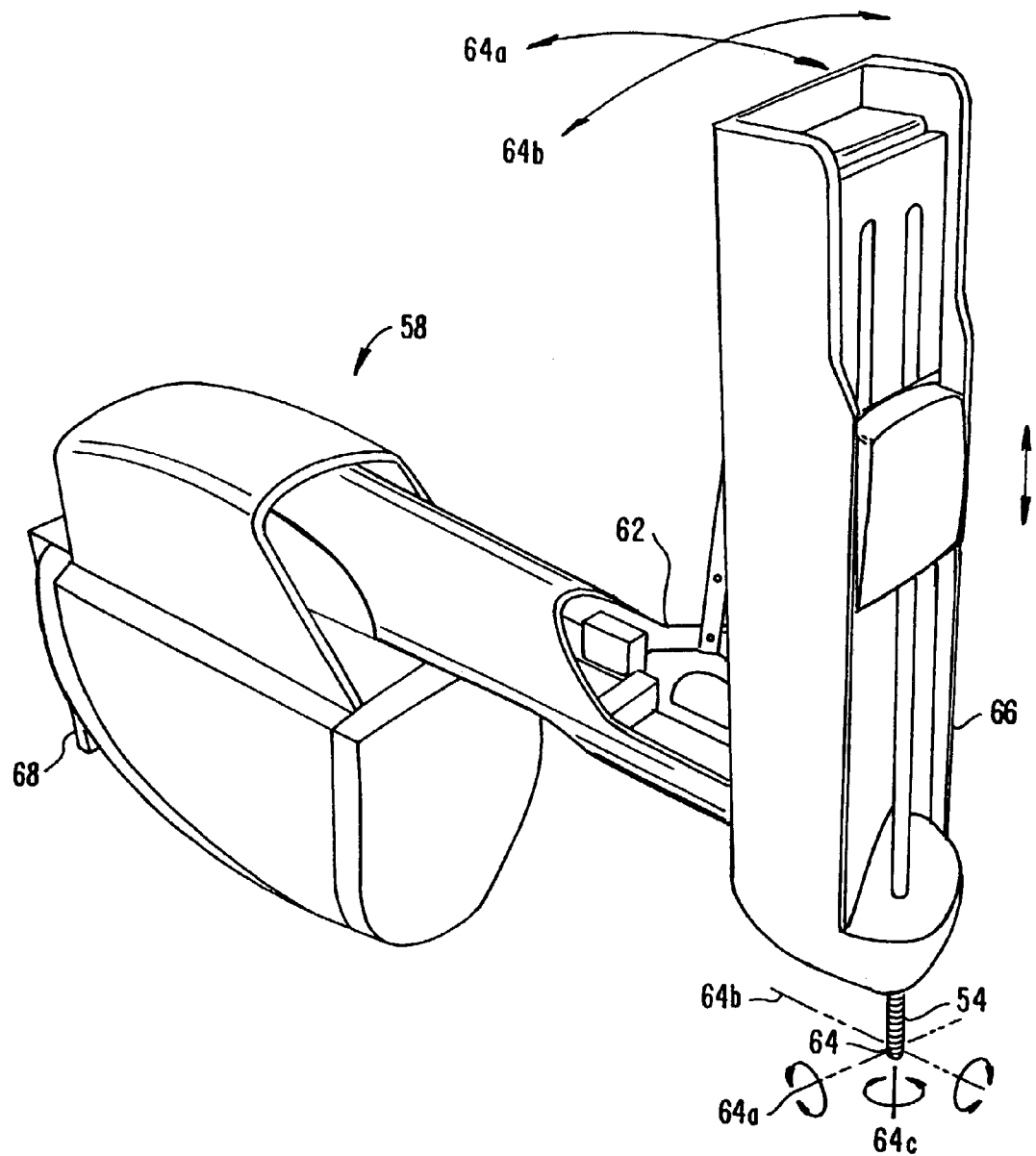
FIG. 2A is a perspective view of a robotic surgical manipulator for use in the cart system of FIG. 2.
Figure 2B:
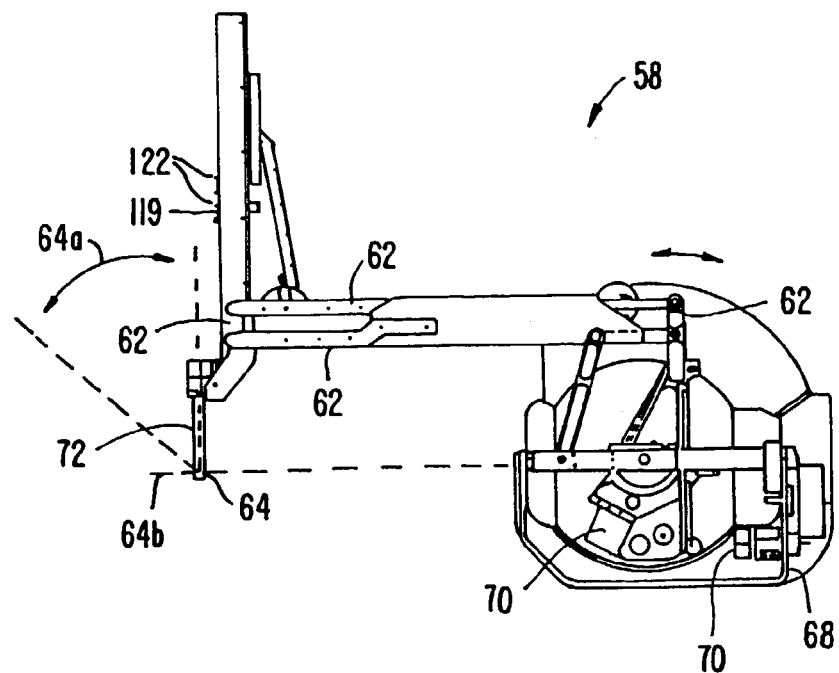
FIGS. 2B and C are side and front views, respectively, of the linkage of the robotic manipulator of FIG. 2, showing how the manipulator maintains a remote center of rotation along a shaft of the surgical tool.
Figure 2C:
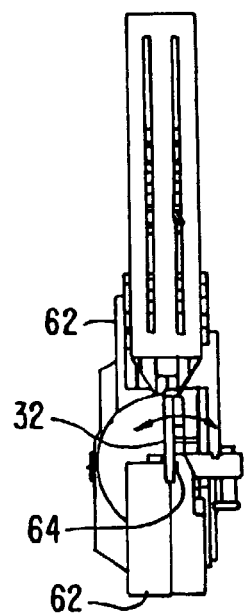

Referring now to FIGS. 2A-C, robotic manipulators 58 preferably include a linkage 62 that constrains movement of tool 54. More specifically, linkage 62 includes rigid links coupled together by rotational joints in a parallelogram arrangement so that tool 54 rotates around a point in space 64, as more fully described in issued U.S. Pat. No. 5,817,084, the full disclosure of which is incorporated herein by reference. The parallelogram arrangement constrains rotation to pivoting about an axis 64a, sometimes called the pitch axis. The links supporting the parallelogram linkage are pivotally mounted to set-up joints 56 so that tool 54 further rotates about an axis 64b, sometimes called the yaw axis. The pitch and yaw axes intersect at the remote center 64, which is aligned along a shaft 66 of tool 54.

Tool 54 has still further driven degrees of freedom as supported by manipulator 58, including sliding motion of the tool along insertion axis 64 (the axis of shaft 66), sometimes referred to as insertion. As tool 54 slides along axis 64c relative to manipulator 58, remote center 64 remains fixed relative to base 68 of manipulator 58. Hence, the entire manipulator is generally moved to re-position remote center 64.

Linkage 62 of manipulator 58 is driven by a series of motors 70. These motors actively move linkage 62 in response to commands from a processor. Motors 70 are further coupled to tool 54 so as to rotate the tool about axis 66, and often to articulate a wrist at the distal end of the tool about at least one, and often two, degrees of freedom. Additionally, motors 70 can be used to actuate an articulatable end effector of the tool for grasping tissues in the jaws of a forceps or the like. Motors 70 may be coupled to at least some of the joints of tool 54 using cables, as more fully described in U.S. Pat. No. 5,792,135, the full disclosure of which is also incorporated herein by reference. As described in that reference, the manipulator will often include flexible members for transferring motion from the drive components to the surgical tool. For endoscopic procedures, manipulator 58 will often include a cannula 72. Cannula 72 supports tool 54, allowing the tool to rotate and move axially through the central bore of the cannula.

Figure 3:
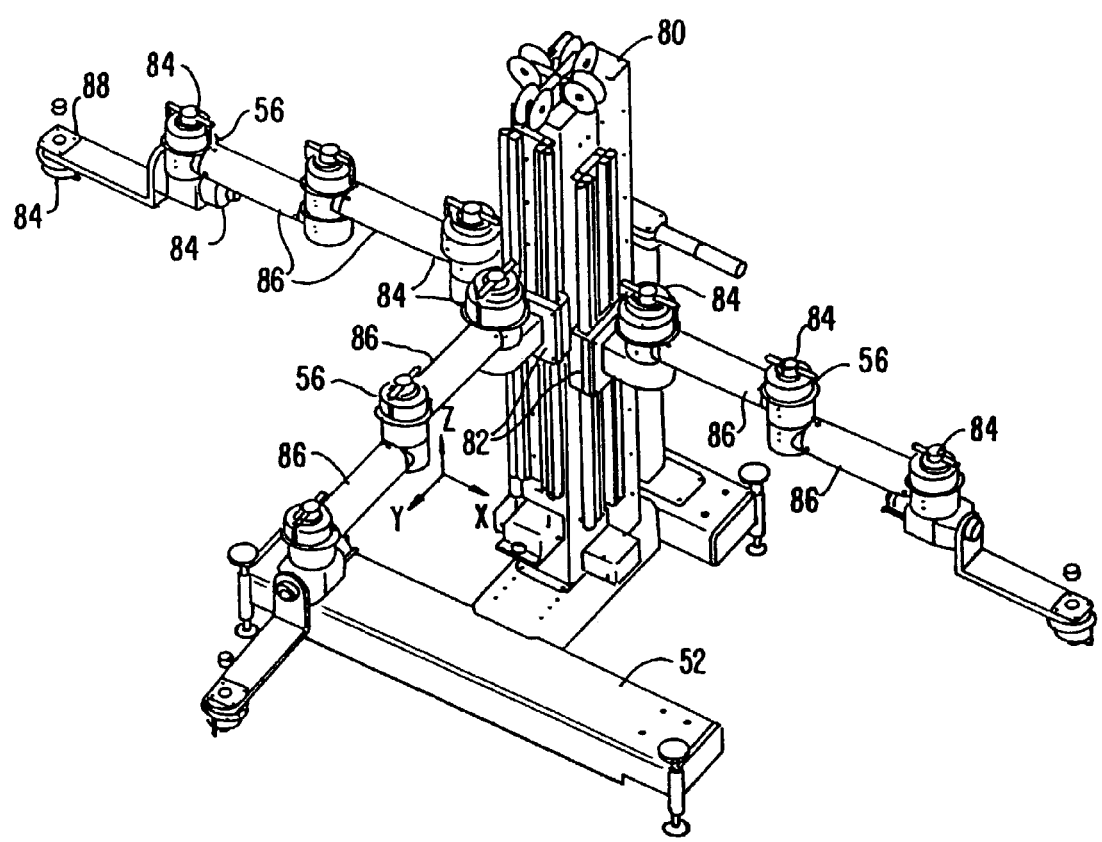
FIGS. 3 and 3A are perspective views of exemplary cart structures with positioning linkages which support the robotic manipulators in the system of FIG. 2.

As described above, manipulator 58 is generally supported by passive set-up joints 56. Exemplary set-up joint structures are illustrated in FIG. 3. The exemplary set-up joint system includes three types of structures. First, a vertical column 80 supports vertically sliding joints 82 that are used to position manipulator 58 along the vertical or Z axis. Second, rotary joints 84 separated by rigid links 86 are used to horizontally position manipulators 58 in the X-Y plane. Third, another series of rotary joints 84 mounted adjacent a manipulator interface 88 rotationally orients the manipulators.

The structure of column 80, vertical sliding joints 82, and base 52 can be understood with reference to FIG. 3. Beginning with base 52, the base will generally distribute the weight of the robotic structures and the forces imposed on the robotic arms. Column 80 extends upward from base 52, and may optionally comprise a box steel structure. Sliding joints 82 are counterbalanced by weights mounted with column 80. Sensors (typically in the form of potentiometers) indicate vertical position of slider joints 82, and also indicate the rotational position of each rotary joint 84. As the structure of the joint elements is known, the processor can accurately determine the position and orientation of the manipulator base. As the position of the tool and tool end effector will be known relative to the manipulator base, the processor can further accurately determine end effector position and orientation, as well as how to effect movement in a desired direction by articulating one or more the driven joints.

Each of rotational joints 84 and slider joints 82 includes a brake. The brake prevents articulation about the joint unless the brake is released, the brake being normally on. The brakes at all the joints are actuated in unison by a button on the set-up joints, thereby allowing the operating room personnel to position the manipulator in space when the brake is released. Additional rotational joints similarly allow the orientation of the manipulator to be set while the brake is released. The exemplary set-up joint structure is more fully described in co-pending application Ser. No. 09/368,309, filed Aug. 3, 1999, the full disclosure of which is incorporated herein by reference.

Figure 3A:
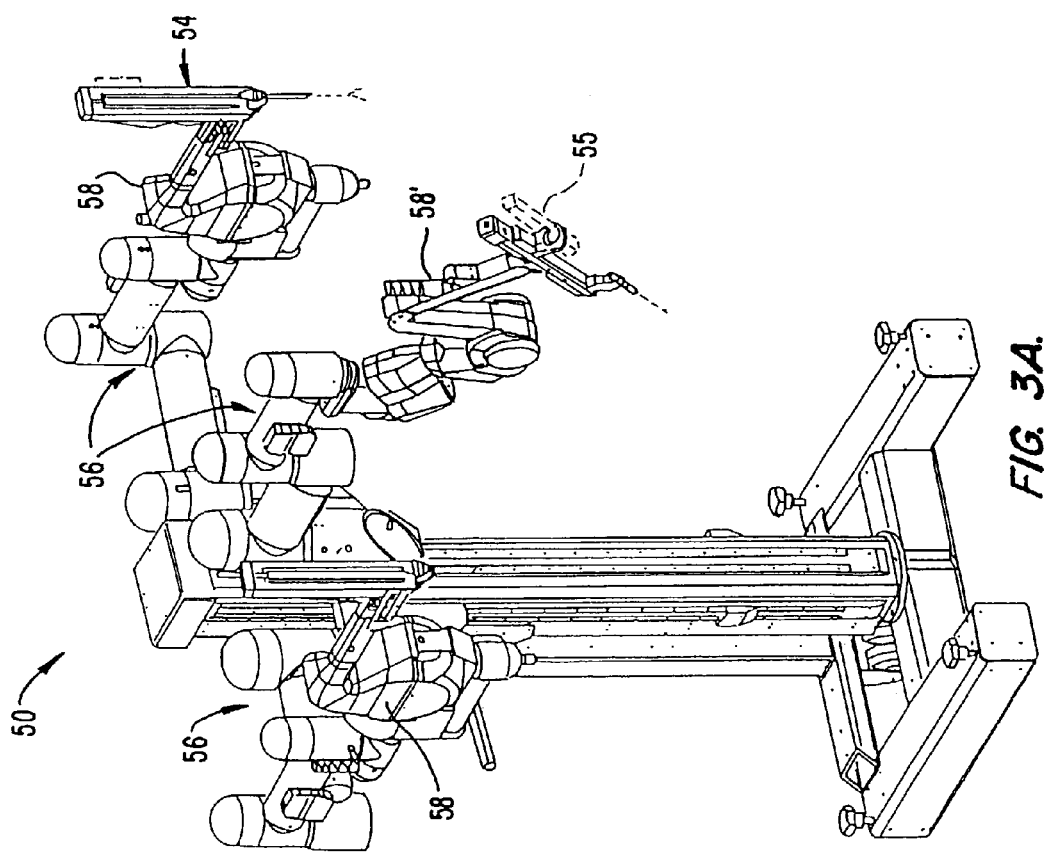

An alternative set-up joint structure is illustrated in FIG. 3A. In this embodiment, an endoscope 55 is supported by an alternative manipulator structure 58' between two tissue manipulation tools. It should be understood that the present invention may incorporate a wide variety of alternative robotic structures, including those described in U.S. Pat. No. 5,878,193, the full disclosure of which is incorporated herein by reference. Additionally, while the data communication between a robotic component and the processor of the robotic surgical system is primarily described herein with reference to communication between tool 54 and the processor of the robotic surgical system, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

An exemplary tool 54 is illustrated more clearly in FIG. 4. Tool 54 generally includes a rigid shaft 102 having a proximal end 104 and distal end 106. A proximal housing 108 includes an interface 110 which mechanically and electrically couples tool 54 to the manipulator. A surgical end effector 112 is coupled to shaft 102 by a wrist joint 114 providing at least 1 degree of freedom, and ideally providing at least 2 degrees of freedom.

As illustrated in FIG. 4A, a drive system 116 mechanically couples first and second end effector elements 112a, 112b to driven elements 118 of interface 110. Drive system 116 is more fully described in U.S. Pat. No. 5,792,135, the full disclosure of which is incorporated herein by reference. Stated simply, the drive system translates mechanical inputs from driven elements 118 into articulation of the wrist about first and second axes A1, A2, as well as into actuation of the two element end effector by relative movement of the end effector elements about axis A2. In addition, driven elements 118 can effect rotation of the end effector about the axis of shaft 102 (A3) by rotating the shaft relative to proximal housing 108, and allowing the cables to twist (within a limited angular range) within the shaft.

Figure 4B:
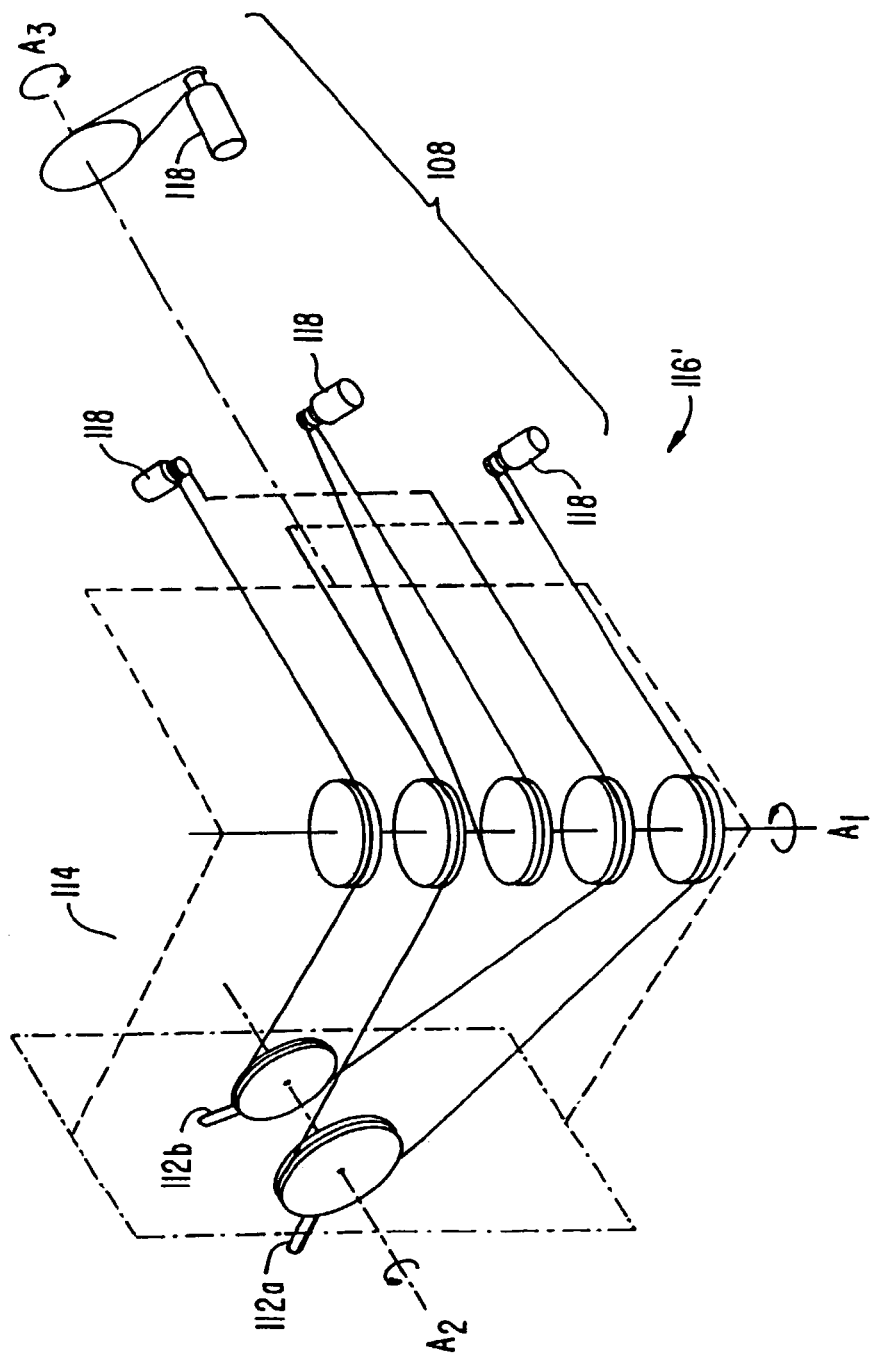
FIG. 4 is a perspective view of an exemplary tool according to the principles of the present invention.
FIGS. 4A and B are schematic views of alternative drive systems for the tool of FIG. 4.

A wide variety of alternative drive systems might be employed, including alternative cabling arrangements, drive chains or belts, hydraulic drive systems, gear trains, or the like. In some of these drive systems, motion of end effector 112 about the axes may be coupled to multiple driven elements 118. In other embodiments, there may be a one to one correspondence between driven elements 118 and motion of an end effector element about an axis. Still other embodiments may require fewer (or more) driven elements to effect the desired degrees of freedom, for example, when a single element end effector is provided. Hence, manipulation of the end effector via interface 110 will generally involve some reconfiguration of the robotic system during the tool change. One alternative drive system 116' is shown in FIG. 4B.

Figure 5A:
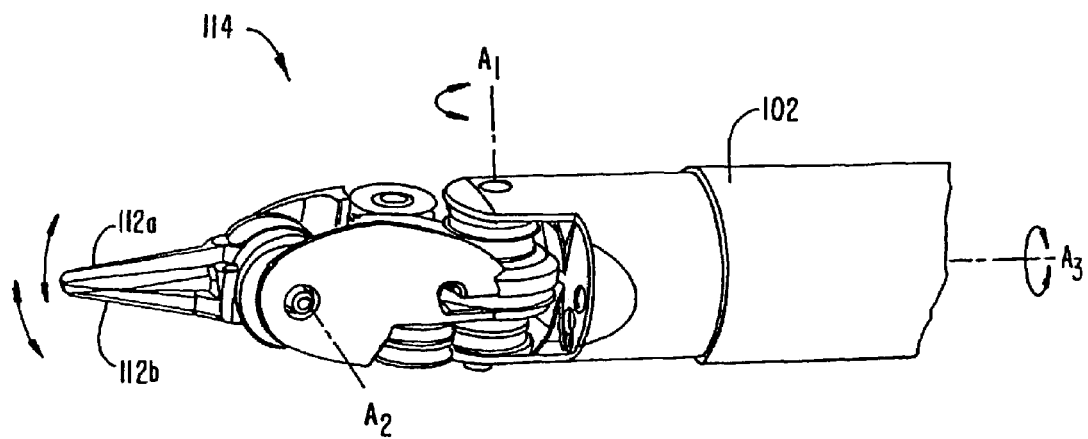
FIGS. 5A through H are illustrations of a variety of surgical end effectors of differing tool-types.
Figure 5B:
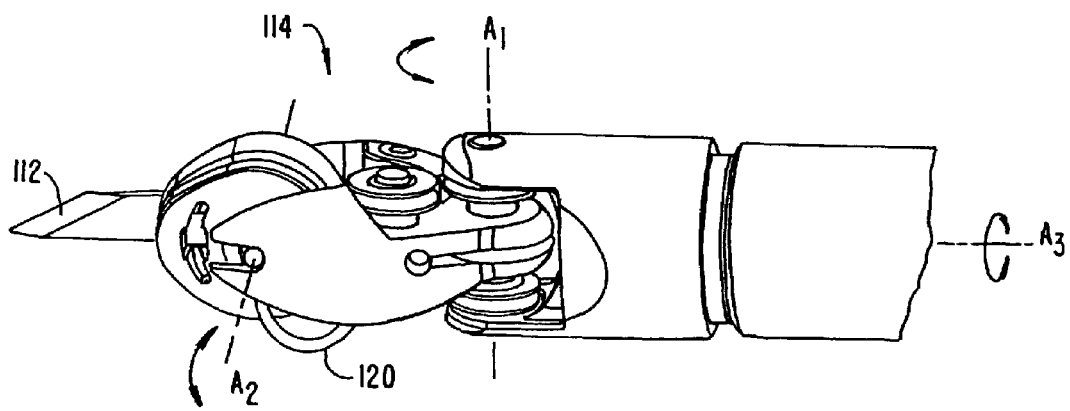

Exemplary wrist structures and surgical end effectors are illustrated in more detail in FIGS. 5A and 5B. A Potts scissor is illustrated in FIG. 5A, while a 15 degree scalpel electrically coupled to a conductor 120 for electrosurgery is illustrated in FIG. 5B. These different tool-types have wrists 114 which may have differing separation distances between their axes A1, A2, differing range of motions about each axes, different joint binding positions or singularities, and/or other differences in their axial geometries. Additionally, these two different end effector structures will have different strengths, different inertias, different effective gearing ratios between motion about their axes and movement of driven elements 118, and the like. Still further differences between these two tool-types, and/or between either of these tools and tools of other types, include the presence or absence of an electrosurgical capability, the useful life of the tool (in time, procedures, or tool change operations), the ability to replace end effector elements, and the like. It should be understood that alternative wrist joint arrangements are possible.

Figure 5C:
Figure 5D:
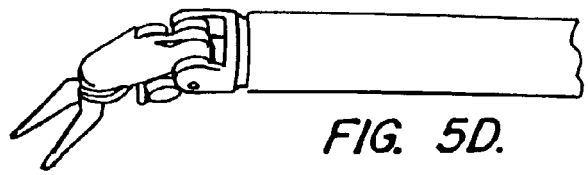
Figure 5E:
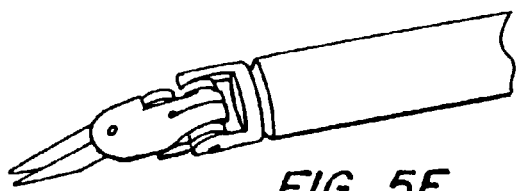
Figure 5F:
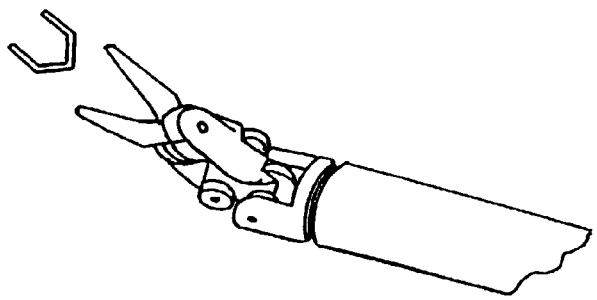
Figure 5G:
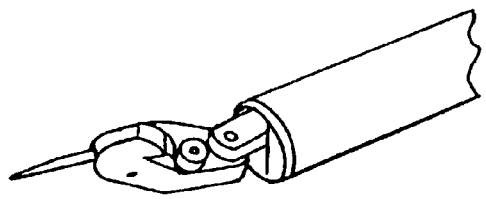
Figure 5H:
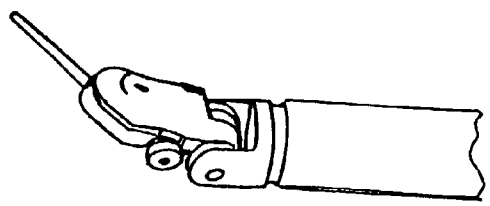

Still further end effectors for additional different tool-types are illustrated in 5C-5H. FIG. 5C illustrates a DeBakey forceps, while FIG. 5D illustrates a microforceps. Potts scissors are again illustrated in FIG. 5E, and a clip applier is illustrated in FIG. 5F. Another scalpel is illustrated in FIG. 5G, while FIG. 5H illustrates an electrocautery probe. It should be understood that a wide variety of alternative end effectors for differing tool-types may be provided, and that several of these tool-types may be used during a single surgical procedure. Hence, the tools of the present invention may incorporate any of the illustrated end effectors, or any other end effector which is useful for surgery, particularly at an internal surgical site.

Figure 6:
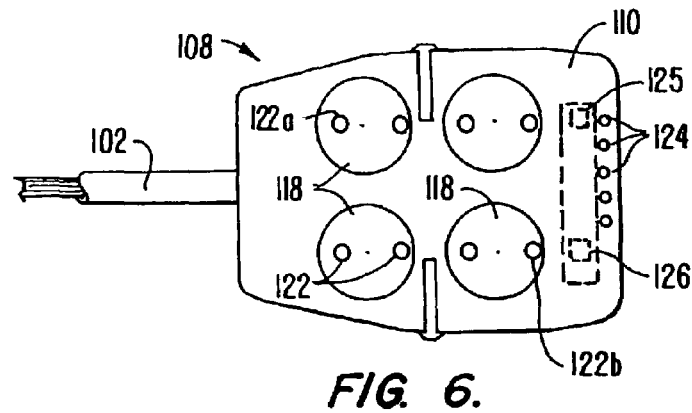
FIG. 6 illustrates the mechanical and electrical interface of the tool of FIG. 4.
Figure 7A:
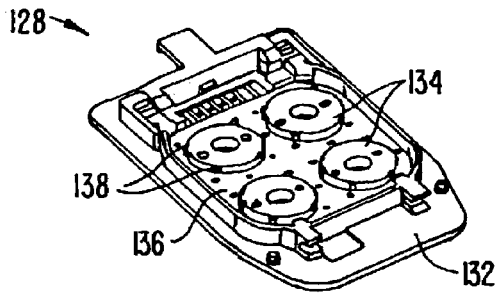
FIGS. 7A through E illustrate an adapter for coupling the interface of FIG. 6 to the surgical manipulator.
Figure 7B:
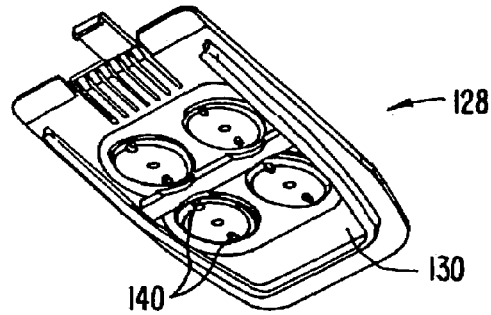
Figure 7C:
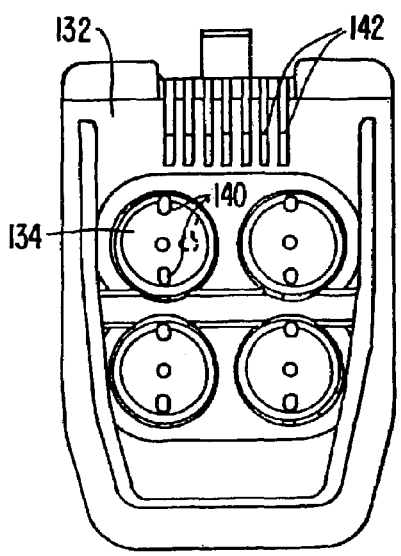
Figure 7D:
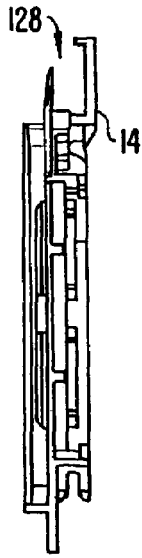
Figure 7E:
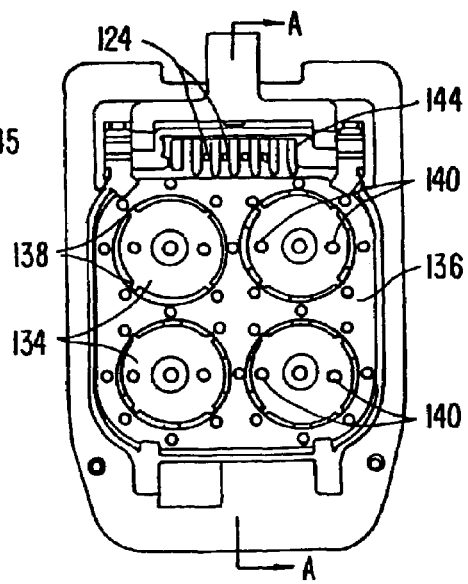
Figure 7G:
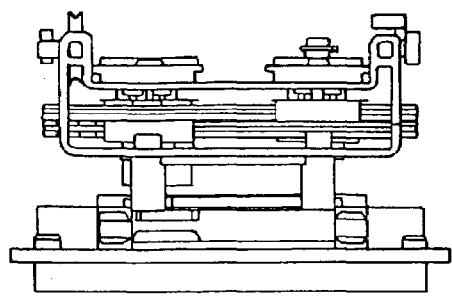
FIGS. 7G through I illustrate the adapter of FIGS. 7A through E mounted to a holder or carriage of the manipulator.
Figure 7F:
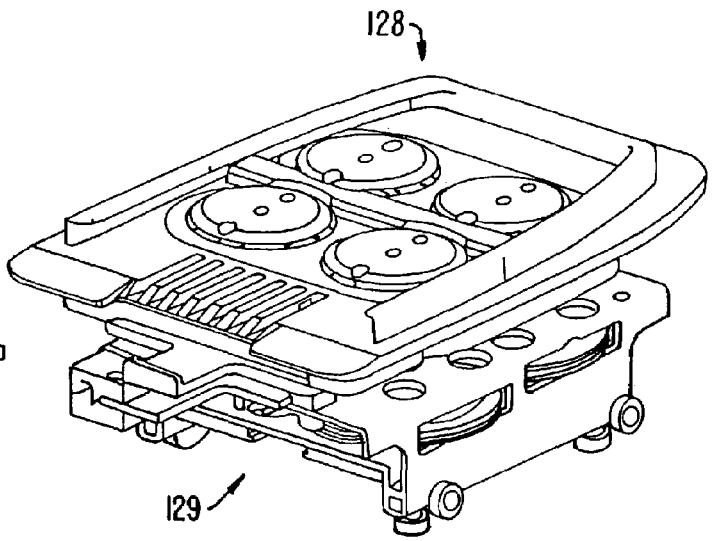
FIGS. 7J through L illustrate the holder, its driving elements, and its electrical contacts.
Figure 7H:
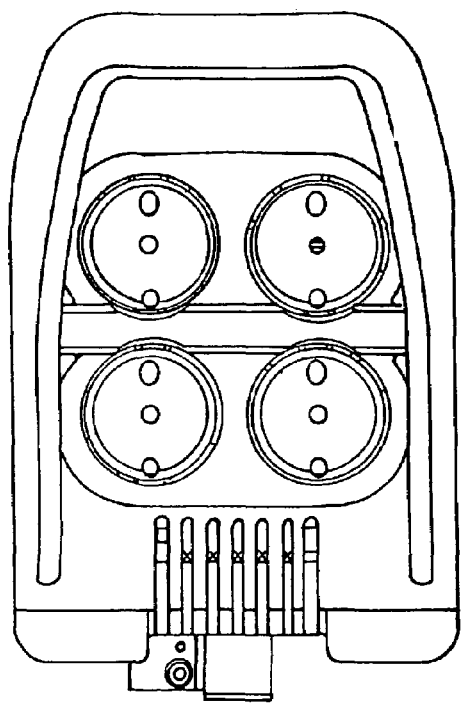
Figure 7I:
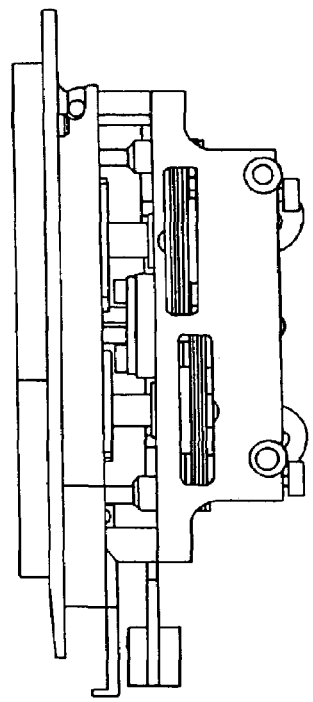
Figure 7K:
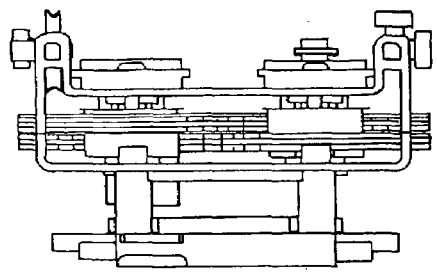
Figure 7J:
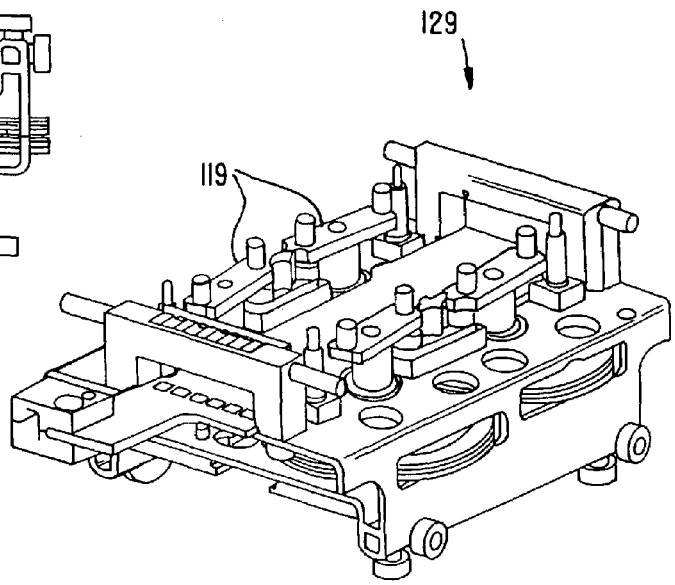
Figure 7M:
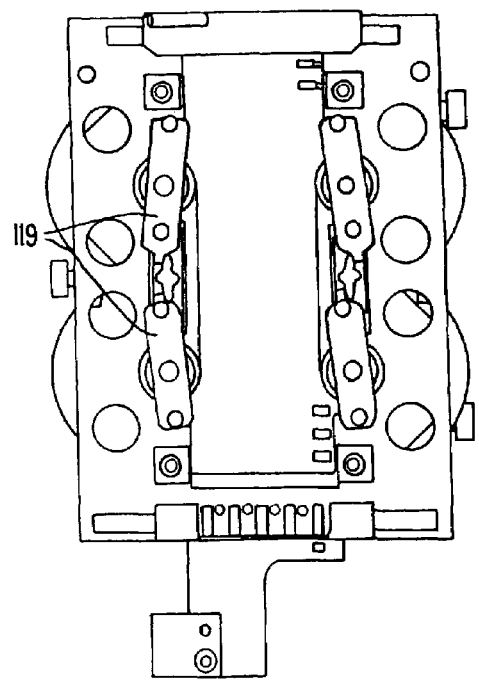
Figure 7L:
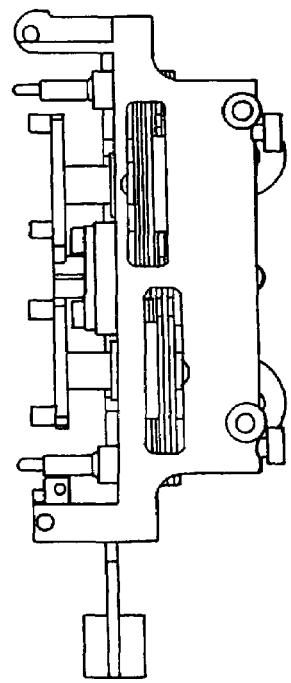

Interface 110 of a proximal housing 108 is illustrated in FIG. 6. As seen schematically in FIG. 4A, driven elements 118 provide mechanical coupling of the end effector to drive motors mounted to the manipulator. Driven elements 118 each include a pair of pins 122 extending from a surface of the driven element. An inner pin 122A is closer to an axis of rotation of each driven elements 118 than an outer pin 122B, which helps to ensure positive angular alignment of the driven element. Interface 110 further includes an array of electrical connecting pins 124 coupled to a memory structure 126 by a circuit board within housing 108. In the exemplary embodiment, memory 126 comprises Dallas part No. DS 2505.

Surgical tools 54 will generally be sterile structures, often being sterilizable and/or being provided in hermetically sealed packages for use. In contrast, the complex servo mechanism of cart 50 and manipulator 58 may be difficult and/or impossible to fully sterilize between procedures. Instead, a sterile drape will often cover at least a portion of the cart and manipulator structures to maintain the sterile environment around the patient.

As tools 54 will be removed and replaced repeatedly during many procedures, the tool holder could potentially be exposed to contamination if the interface directly engages the tool holder. To avoid contamination of the tool holder and possible cross contamination between patients, the present invention provides an adaptor for coupling interface 110 to the tool holder of the manipulator assembly.

White interface 110 is described herein with reference to mechanical, electrical, and magnetic coupling elements, it should be understood that a wide variety of telemetry modalities might be used, including infrared, inductive coupling, or the like.

Referring to FIGS. 7A-7E, adaptor 128 generally includes a tool side 130 and a holder side 132. A plurality of rotatable bodies 134 are mounted to a floating plate 136 which has a limited range of movement relative to the surrounding adaptor structure normal to the major surfaces of the adaptor. Axial movement of the floating plate helps decouple the rotatable bodies from the tool when the levers along the sides of housing 108 are actuated (See FIG. 4).

Rotatable bodies 134 are resiliently mounted to floating plate 136 by resilient radial members which extend into a circumferential indentation about the rotatable bodies. The rotatable bodies can move axially relative to plate 136 by deflection of these resilient structures.

When disposed in a first axial position (toward tool side 132) the rotatable bodies are free to rotate without angular limitation. However, as the rotatable bodies move axially toward tool side 130, tabs 138 (extending radially from the rotatable bodies) laterally engage detents on the floating plates so as to limit angular rotation of the rotatable bodies about their axes. This limited rotation can be used to help drivingly engage the rotatable bodies with drive pins of the holder, as the drive pins will push the rotatable bodies into the limited rotation position until the pins are aligned with (and slide into) openings 140.

Openings 140 on the tool side 130 and holder side 132 of rotatable bodies 134 are configured to accurately align the driven elements 118 of the tool with the drive elements of the holder. As described above regarding inner and outer pins 122A, 122B of driven elements 118, the openings 140 in each side of each rotatable body are at differing distances from the axis of rotation so as to ensure that the alignment is not 180° from its intended position. Additionally, each of the openings 140 is slightly radially elongate so as to fittingly receive the pins in the circumferential orientation. This allows the pins to slide radially within the openings and accommodate some axial misalignment between the tool and holder, while minimizing any angular misalignment and backlash between the drive and driven elements. Openings 140 on the tool side 132 are offset by about 90° from the openings on the holder side, as can be seen most clearly in FIG. 7C.

Holder side of adaptor 128 includes another array of electrical connector pins 124, and the tool side 132 of the adaptor includes slots 142 for receiving the pin array from the tool (as illustrated in FIG. 6). In addition to transmitting electrical signals between the tool and holder, at least some of these electrical connections are coupled to an adaptor memory device 144 by a circuit board of the adaptor. A latch 145 releasably affixes the adaptor to the holder. A lip on the tool side 130 of adaptor 128 slidably receives laterally extending tabs of housing 108 adjacent to interface 110. The interaction between pins 122 and openings 140 helps restrain the tool in the engaged position until the levers along the sides of the tool housing push the floating plate axially from the interface so as to release the tool. The holder 129 and drive elements 119 are shown (without the adjacent manipulator structure) in FIGS. 7F through M.

Figure 8B:
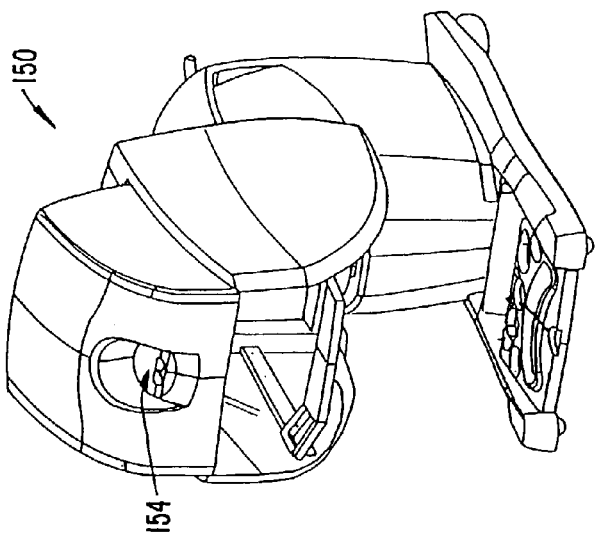
FIG. 8 is a wiring diagram for the tool of FIG. 4, the adapter of FIG. 7A-E, and related components of the robotic system.
FIGS. 8A and B are rear and front views of the master console, respectively.
Figure 8:
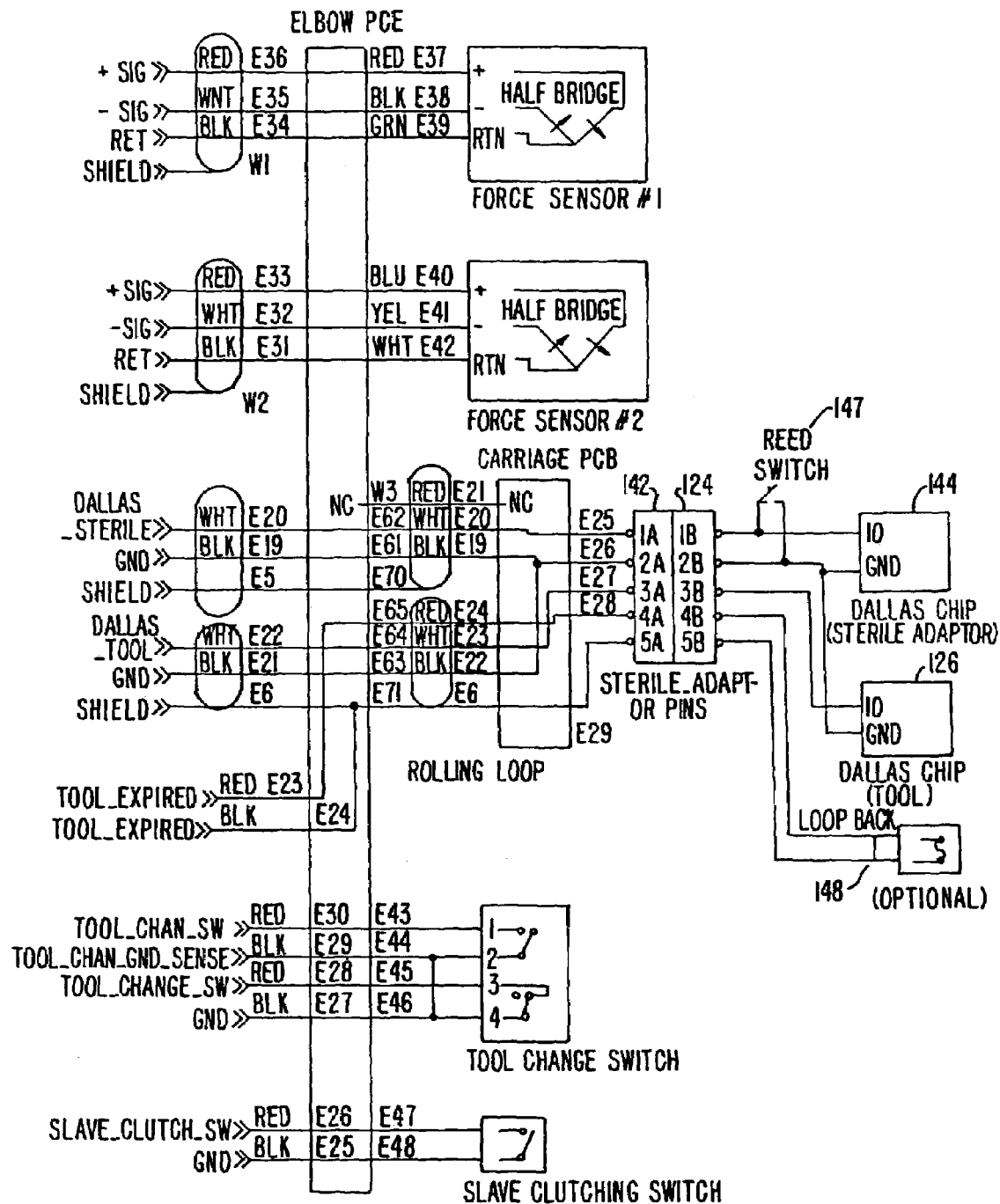

Referring now to FIG. 8, an exemplary circuit diagram illustrates the coupling of tool memory 126 and adaptor memory 144 to the wiring harness of the manipulator. The electrically coupling of tool memory 126 with the wiring of the manipulator may be used to sense the presence of the tool. Similarly, electrical coupling between the manipulator wiring system and adaptor memory 144 may be used as an adaptor engagement sensor. In the exemplary embodiment, two additional sensors are also provided to determine engagement of the tool and holder: a magnetic reed switch 147 (actuated by a magnet 125 of interface 110), and a electrical coupling short 148 (or alternatively an end-of-life indicator) electrically coupling two of the pins 124 of tool 54. The use of a magnetically actuated sensor mounted to the holder or adapter is particularly advantageous. The tool-mounted magnet will tend to maintain the signal from a magnetic sensor (despite small, stress induced movements of the tool), in part because of the magnetic field effects and/or hysteresis, once contact has been made. Optionally, adapter memory 144 may be read only when no tool is coupled to the adapter by "shorting" the adapter memory with the magnetic reed switch, so that the adapter is transparent to tool/processor communications after installation is completed.

Figure 8A:
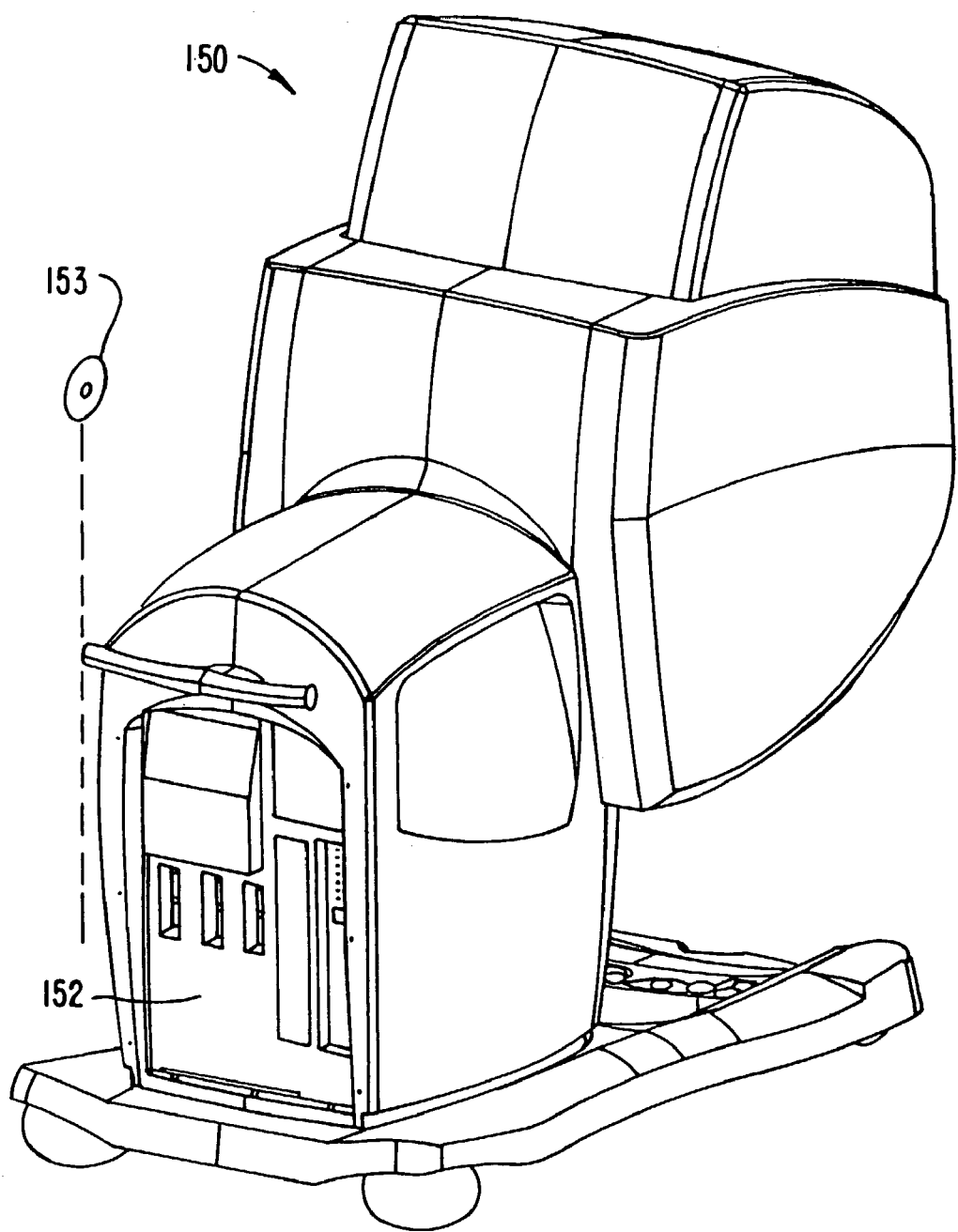

An exemplary surgeon's workstation is illustrated in FIGS. 8A and 8B. Control station 150 includes processors 152 for the robotic circle mechanism. Also included in controller station 150 are a stereo imaging system 154 and a pair of controllers (not shown).

The surgeon will generally manipulate tissues using the robotic system by moving the controllers within a three dimensional controller work space of controller station 150. Processor 152 can calculate an image capture coordinate system via the sensors in setup joints 56 and manipulator 58 supporting the laparoscope, and can perform coordinate system transformations so as to generate signals to the drive motors of the manipulator that maintain alignment between the three dimensional image of the end effectors and the hand controllers within the controller work space. By maintaining this alignment, as the physician moves the hand controller in both position and orientation, the robotic surgery system allows the surgeon to manipulate the surgical tools as if the handle in the surgeon's hand and the end effector in the surgeon's field of view define a single contiguous surgical instrument. This provides an enhanced sense of presence and allows the surgeon to operate efficiently and accurately without performing mental coordinate transformations. The program instructions for effecting these processes may optionally be embodied in a machine readable code stored on a tangible media 153, which may comprise an optical disk, a magnetic disk, a magnetic tape, a bar code, EEPROM, or the like. Alternatively, programming instructions may be transmitted to and from processor 152 using data communications systems such as an IO cable, an intranet, the internet, or the like. An exemplary control system is described in more detail in co-pending U.S. patent application Ser. No. 09/373,678, filed Aug. 13, 1999, for a Camera Referenced Cartesian Control System, the full disclosure of which is incorporated herein by reference.

Figure 9:
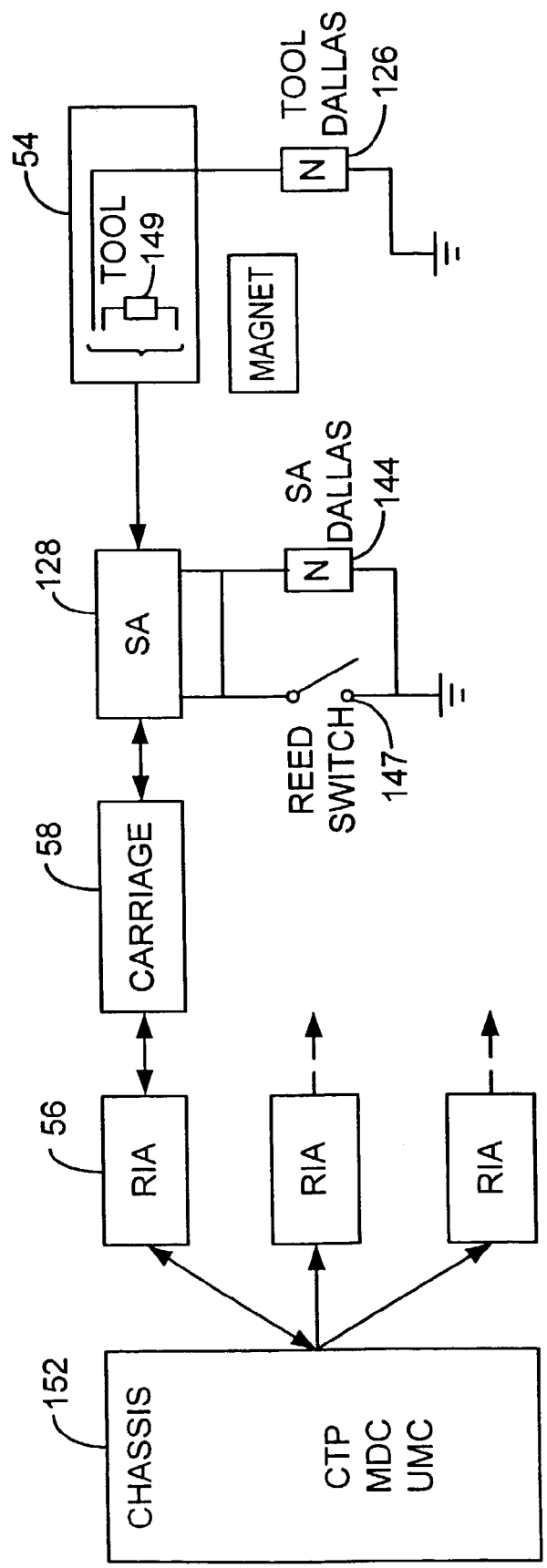
FIG. 9 is a functional block diagram schematically illustrating the signal path hardware of the tool change system.

The tool/adaptor hardware signal path is schematically illustrated in FIG. 9. Processor 152 of master control station 150 comprises multiple separate processor boards supported by a chassis. In the exemplary embodiment, a control and transform processor CTP handles calculation of the coordinate system transforms for generating the proper instruction signals to send to servo motors. The control and transform processor CTP may comprise an Analog Device ADSP 21060 digital signal processor, or a wide variety of alternative commercially available processors. A master diagnostic controller MDC monitors and verifies the health of the processing and servo mechanical system. In the exemplary embodiment, the master diagnostic controller MDC comprises a Dallas DS 87C530 processor. A Dallas DS 87C520 processor is used as the user interface master controller UMC to handle the input and output to and from the surgeon seated at the console. Once again, these functions may alternatively be performed by a variety of commercially available processors. Hence, processor 152 may include a single processor, or a number of distinct processor structures coupled together, ideally in a distributed processing arrangement.

In the exemplary distributed processing arrangement shown in FIG. 9, processor 152 makes use of a remote printed circuit assembly ("PCA") referred to as the remote interface adaptor RIA, which is coupled to the chassis by a wiring harness. A remote interface adaptor RIA is provided for each of the robotic arms of the system, typically including one PCA for the endoscope and two PCA's for the two surgical end effectors. The remote interface adaptor RIA also comprises a Dallas DS 87C 520 processor and couples the processor 152 to the holder or carriage of manipulator 58. The RIAs 56 perform local processing for the manipulators, setup joints, and/or tools, and communicate with processor 152 using a high-level language. Manipulator 58 is, in turn, coupled to tool 54 by adaptor 128 as described above.

It should be noted that reed switch 147 may actually be mounted on carriage of manipulator 58, and may be actuated by a magnet mounted on the tool 54. Hence, reed switch 147 ensures that tool 54 is positioned in the holder of manipulator 58, the reed switch acting as a tool sensor. Electrical coupling of the tool memory 126 and an electrical loop-back circuit 149 connecting pins of tool 54 each act as additional independent tool sensors. Optionally, an end-of-use detector such as a low resistance timed fuse, or the like, may change an electrical characteristic of the loop-back circuit to disqualify tools past the end of their safe lives. An expired tool may provide an indication to the system operator such as a pop-up flag, a color-change spot, or the like, to indicate the tool is at or near the end of its life. Optionally, a portable life indication device may be coupled to the tools before each procedure to determine if the tool has sufficient life to be used for the planned procedure.

A variety of alternative end of use indication systems might be provided to indicate that a tool is near or at the end of its useful life. For example a mechanical end of use indicator may be mounted in housing 108, such as a colored button or tab which can pivot into view through an indication window of the housing. Such a button might be biased toward the viewable position, and initially held out of sight by a latch. The latch might be releasable by an actuator mounted to the carriage of manipulator 58, for example, by the movement of a plunger of a solenoid on the manipulator. The sterile adapter or drape will preferably accommodate movement of such a plunger while maintaining sterile separation between the manipulator and tool. In general, providing a mechanical indicator on the tool for actuation by an actuation means of the manipulator can avoid the cost for end of use actuators mounted on each tool.

Figure 10:
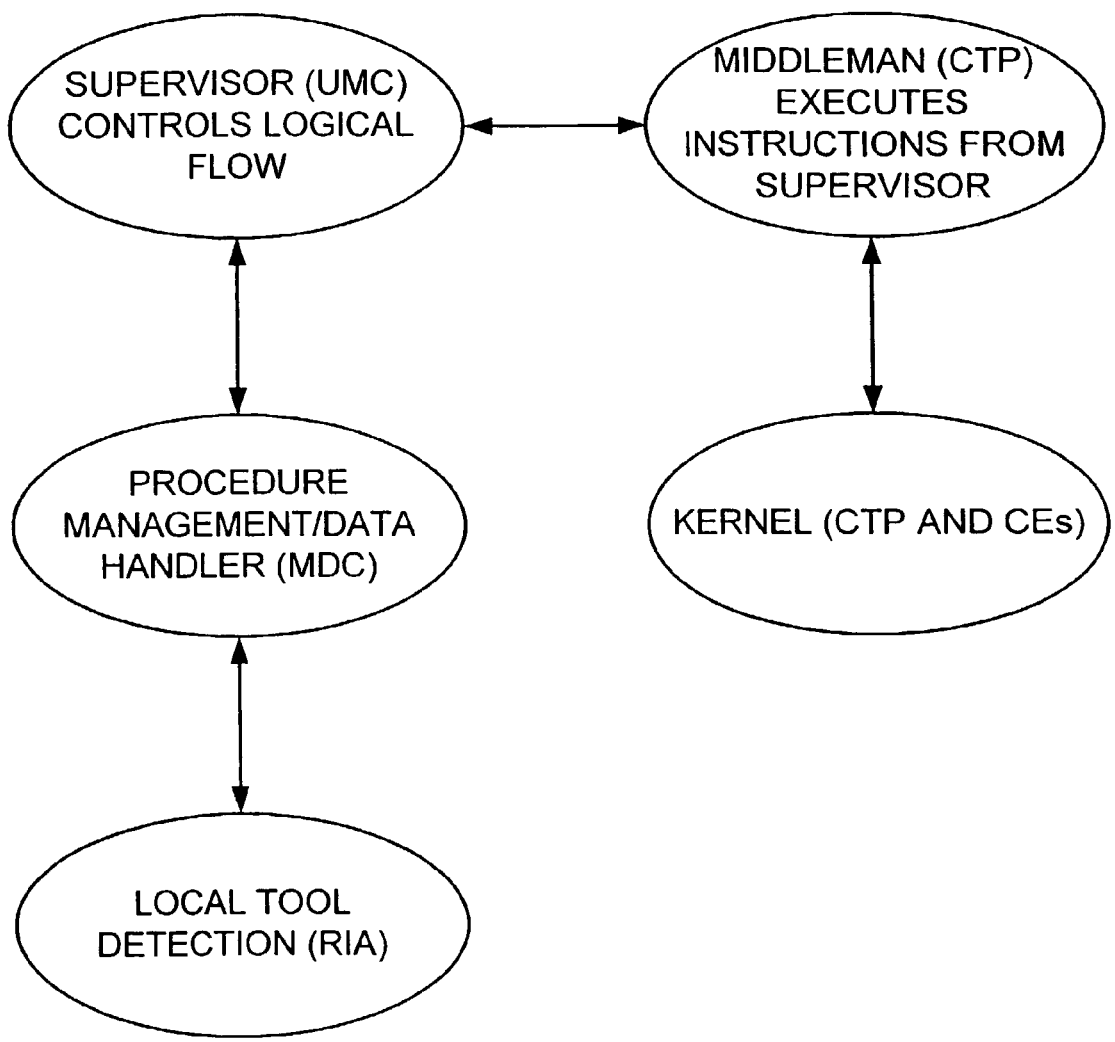
FIG. 10 is a schematic diagram illustrating the interaction between the software modules related to tool change.

Referring now to FIG. 10, the flow of the tool signals from the tool sensors during a tool change operation originates from the interaction between the remote interface adaptor RIA and the tool itself. The tool signals are transmitted per procedure management/data handler programming running on the master diagnostic controller MDC. The overall logic flow proceeds according to a supervisor program running on the user interface master control UMC according to the surgeon's input from the master console.

The supervisor directs the state of the robotic arms, and also perfects coupling between a mounted tool 54 and the holder of a manipulator by driving the servo motors in a predetermined manner, as shall be explained below. The supervisor software directs movement of the tool through a middleman program running on the control and transform processor CTP. The middleman program accepts instructions from the supervisor to move the surgical end effectors in the desired direction, for example, and calculates the drive signals to be provided to the servo motors so as to effect that desired motion. In other words, the middleman program transforms the workstation space instruction into a joint space servo signal set for the servo motors to drive the end effectors.

It should be understood that the coordinate transformations used by the middleman to calculate the required servo signals will vary as the relationship between the field of view from the endoscope and the surgical end effectors varies. Deriving these coordinate transformations is well described in the patent literature, for example, in U.S. Pat. No. 5,696,837 and U.S. patent application Ser. No. 09/373,678, the full disclosures of which are incorporated herein by reference. In the control method illustrated in FIG. 10, a Kernel program running on the control and transform processor CTP and Compute Engine processors CE's derives these transformations based on the information provided by the position sensors at the setup joints, manipulators, and the like.

Figure 11:
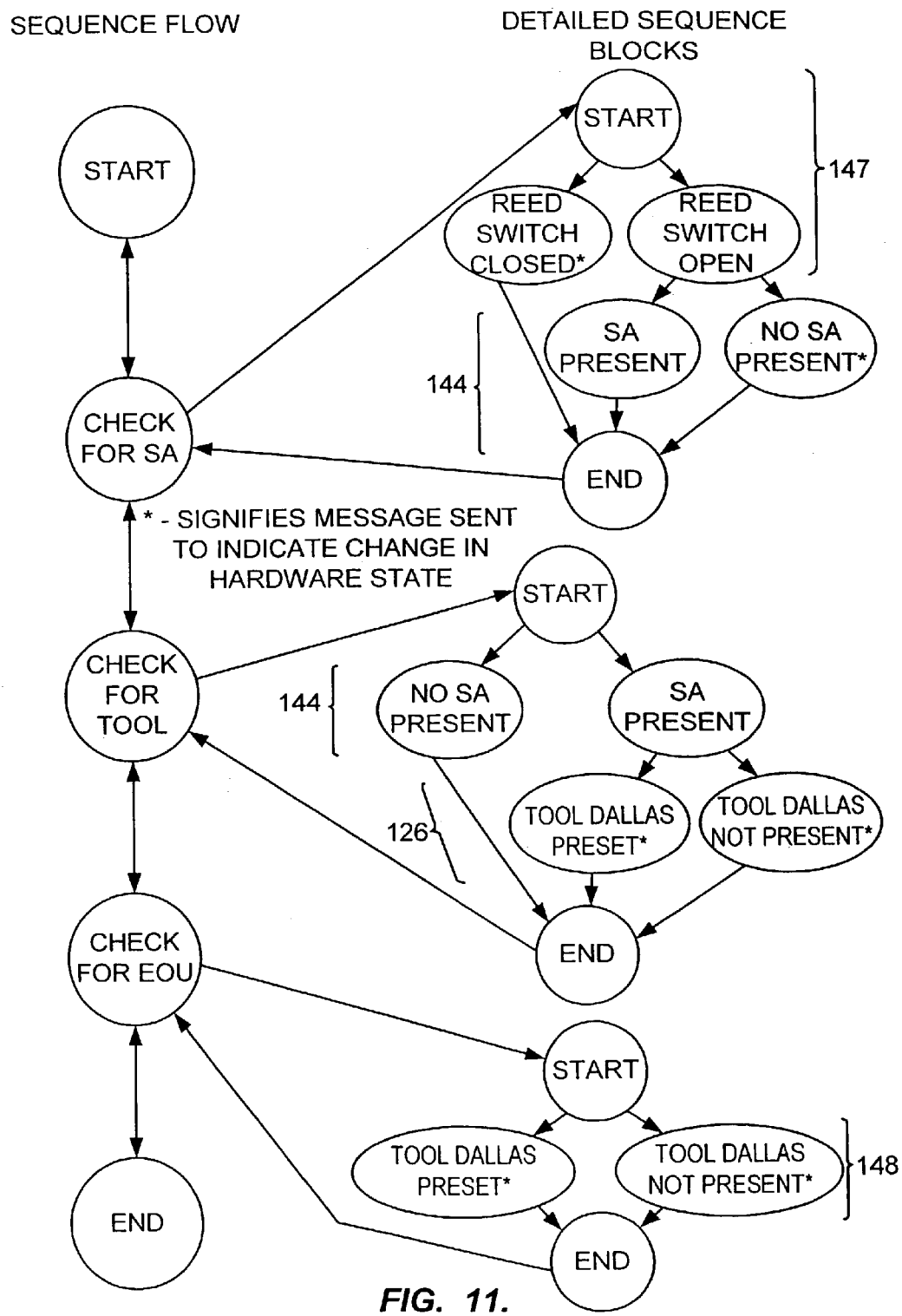
FIG. 11 is a logic flow chart illustrating an exemplary method for sensing engagement of a tool with the manipulator.
Figure 12:
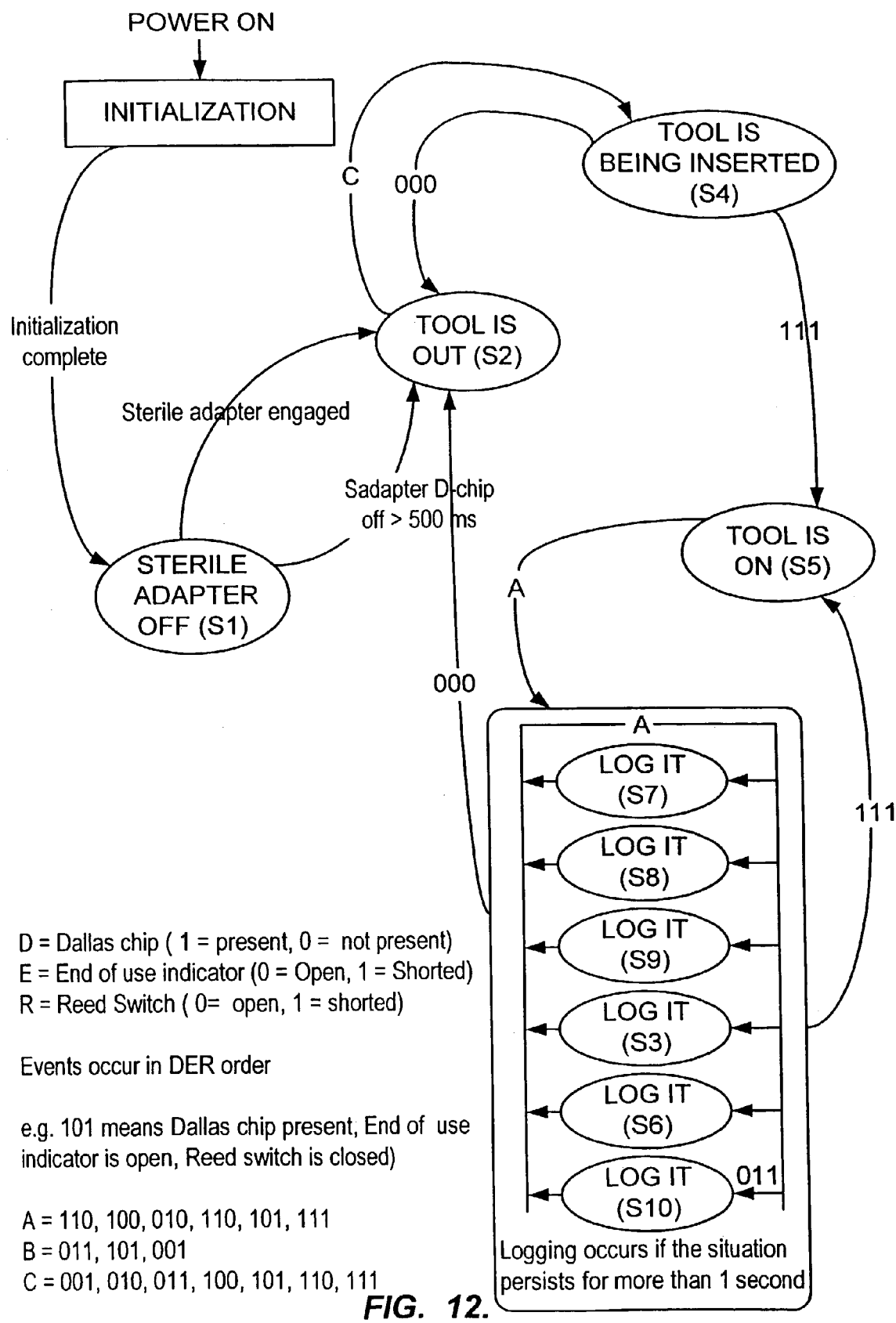
FIG. 12 is a flow diagram illustrating how the tool engagement signals are used to change the operating state of the robotic system.

Referring now to FIGS. 11 and 12, processor 152 changes the operating state of the robotic system based on tool signals from the three tool engagement sensors (reed switch 147, tool memory 126, and end of use/pin short circuit 148) and an adaptor signal sensed by coupling with the adaptor memory 144. In the local tool detection procedure illustrated in FIG. 11 (which is performed at the remote interface adapter RIA with a cycle time of 35 milliseconds) the reed switch and adapter memory are first sensed to check for the presence of the adapter. So long as the adapter is present, the system then checks for the presence of the tool based on coupling with the tool memory 126. The presence or absence of the tool is verified by checking for the end of use or pin short circuit 148 of the tool breadboard. The remote interface adapter RIA transmits the sensed signals from the sensor scan to the master digital controller MDC for use by the Procedure Management/Data Handler software.

As can be understood with reference to FIG. 12, if the sterile adapter is not sensed (either upon start up or while the tool is removed), the robotic system remains in a sterile adapter off operating state S1. Once the sensor scan indicates that adapter 128 is present, program management data handler advances the operating state to a second operating state S2 in which the system is awaiting engagement of interface 110 with the holder of the manipulator. If the signal from the adapter memory chip is lost for more than half a second, the system returns to the adapter off state S1.

If at least one signal from the three tool sensors indicates engagement of the tool, the operating state advances to a Tool Being Inserted mode S4, and upon agreement of all three sensors that the tool is fully mounted on the holder, the system enters a Tool Is On operating state S5 in which manipulation of the end effectors by the surgeon may be enabled.

The elongate shafts of tool 54 can induce significant mechanical stresses between interface 110, adapter 128, and the holder of the manipulator. As a result, one or more of the tool signals may be lost at least temporarily. If tissue manipulation were halted each time a tool signal were lost, the operation would be significantly delayed and total risk to the patient would increase. The present system takes advantage of the redundant tool signals by keeping the system in the Tool Is On operating state S5 despite the loss of one or even two tool signals. If the loss of signal persists for more than a threshold time, the signal loss is stored for diagnostic purposes. Nonetheless, the system remains in the operating state, until all three tool signals indicate the tool is removed, at which point the system drops down to the Tool Is Out operating state S2. This procedure provides a much more robust approach than analyzing each tool signal independently.

Figure 13:
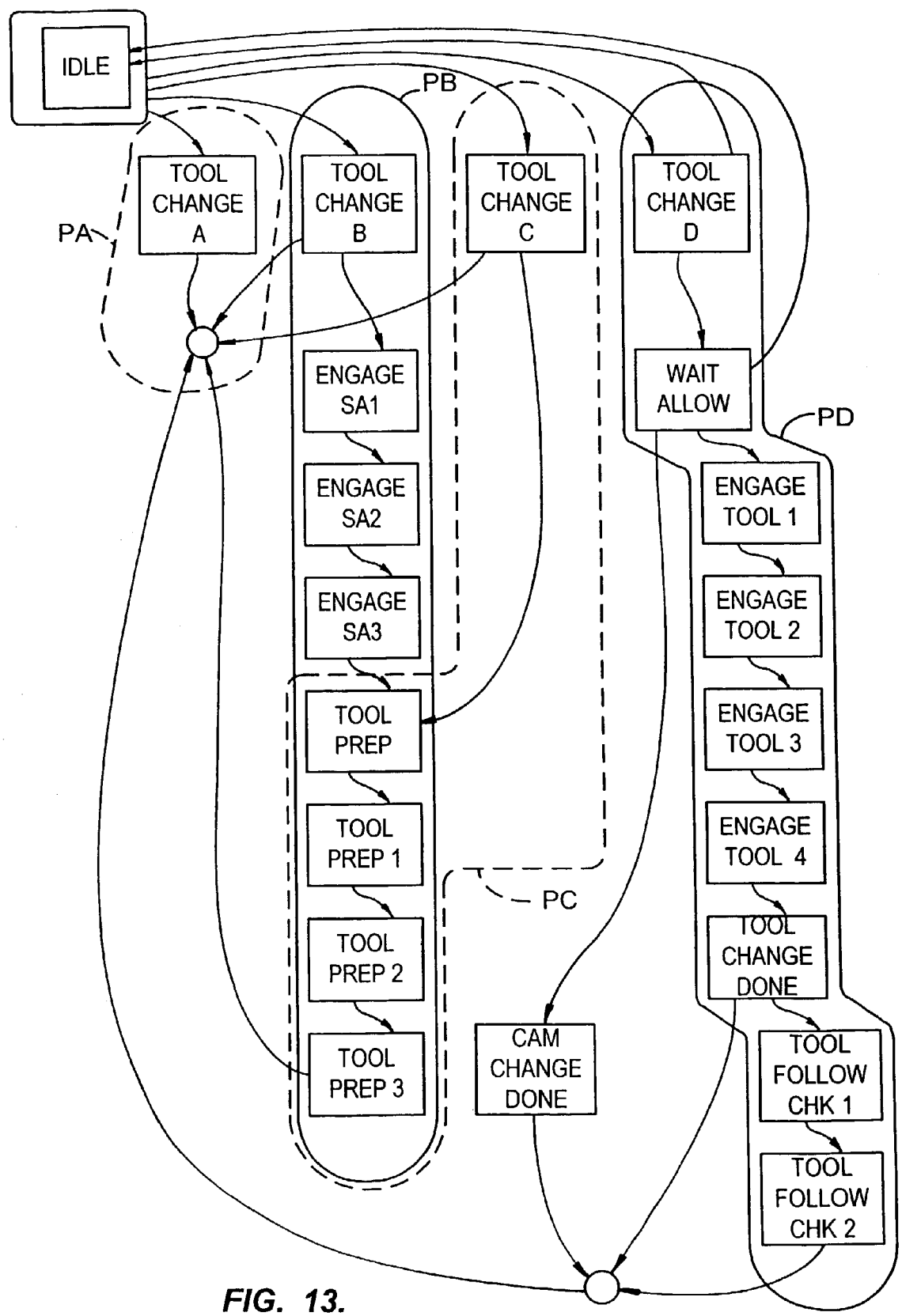
FIG. 13 illustrates the tool engagement method steps initiated by the processor in response to a change in operating state during tool changes.

Referring now to FIG. 13, the instructions generated by the supervisor software running on the user interface master controller UMC as a result of the changes in state during a tool change procedure will generally follow one of four paths. If the adapter is not present and a tool has been taken off (or no tool and adapter are present at start up), the supervisor notifies the user, for example, by displaying an icon on the stereo display and/or assistance monitor, per path PA. If an adapter has been mounted to the holder and no tool is engaged, the supervisor initiates manipulations of the driving elements of the holder which perfect mechanical coupling of the rotational bodies of adapter 128 with the driving elements of the holder per path PB.

As described in some detail with reference to FIGS. 7A through E, rotatable bodies 134 can move axially relative to a floating plate 136. Prior to perfecting mechanical coupling between the holder drive elements and the rotatable bodies, pins of driving elements (which are similar in configuration to the driven elements 118 of interface 110) will push the rotatable bodies away from holder side 132 of adapter 128 and toward tool side 130. In this rotationally limited axial position, tabs 138 of rotatable bodies 134 engage detents of the floating plate so as to prevent rotation of more than about 90°. This can ensure that the pins of the driving elements rotate relative to the rotatable bodies by driving the servo motors of the manipulator by more than 90°.

In the exemplary tool change engagement path PB, the servo motors of the manipulator are driven from a starting central position so as to rotate the drive elements by 180° in a first direction (for example, clockwise) in step ENGAGESA1. As the pins of the driving elements will only enter opening 140 of rotatable bodies 134 in a single angular orientation, it is possible that this step will be insufficient to perfect mechanical coupling. To ensure that coupling is complete, the supervisor therefore initiates rotation of the servo motors so as to turn the driving the elements by 360° in the opposite direction (in our example, counterclockwise) in step ENGAGESA2. At some point during the above two steps, pins 122 of the driving elements will be aligned with openings 144 of rotatable bodies 134 and the openings will receive the pins, thereby allowing the rotatable body to move axially to the freely rotatable position. The driving elements in rotatable bodies are then centered in their range of angular travel in step ENGAGESA3.

Once the steps of path PB have been performed so as to perfect mechanical coupling of the driving elements of the holder with the rotatable bodies of the adapter 128, the supervisor directs the system to perform the procedure outlined by the second part of path PB. Basically, the driving elements (and rotatable bodies) are centered and centering is verified in preparation for mounting of a tool to the holder by rotating the servos right to their end of travel, left, and then halfway between under steps TOOLPREP1, 2, and 3, respectively. These centering and verification steps are also performed if a tool has been removed from the holder, per path PC.

In the final alternative procedure which will be described with reference to FIG. 13, mounting of a tool on the adapter and holder results in the steps outlined in path PD. First, the system verifies that the tool is of the type which is allowable for use on this particular robotic surgical system. To determine compatibility, circuitry of the tool may send a signal indicating the tool-type to processor 152. More specifically, data stored in tool memory 148 may be transmitted to the processor. In the exemplary embodiment, the data from the tool memory will include a character string indicating tool compatibility with the robotic system. Additionally, the data from the tool memory will often include a tool-type. In some embodiments, the data will also include tool offset calibration information. This data may be provided from the tool memory 148 in response to a request signal from the processor 152. A simplified version of path PD is performed if a camera is changed, as shown.

Tool-type data will generally indicate what kind of tool has been attached in a tool change operation. For example, the tool-type data might indicate that Potts scissors or a scalpel has been attached to the holder. The tool-type data may include information on wrist axis geometries, tool strengths, grip force, the range of motion of each joint, singularities in the joint motion space, the maximum force to be applied via driven elements 118, the tool transmission system characteristics including information regarding the coupling of driven elements 118 to articulation of an associated (or the interacting plurality of associated) joint motion, servo gains, end effector elements speeds, and the like.

Tool-type data may optionally be stored in memory of the robotic system. The signal from the tool may comprise an identifier referencing the relevant portion of data from the look-up table. This tool-type data may be loaded into a memory of processor 152 by the system manufacturer, the look-up table preferably being in the form of a flash memory, EEPROM, or the like. As each new tool-type is provided, the robotic system manufacturer can then revise the look-up table to accommodate the new tool-specific information. It should be recognized that the use of tools which are not compatible with the robotic surgery system, for example, which do not have the appropriate tool-type data in an information table, could result in inadequate robotic control over the end effector by both processor 152 and the surgeon.

In addition to the tool-type data indicated by the signals from tool 54, tool specific information may be stored in the tool memory 148 for reconfiguring the programming of processor 152. For example, there will often be some measurable misalignment or offset between and intended relationship between the wrist joint and end effector elements and the positions of driven elements 118. To accommodate this misalignment without degrading the accuracy of the robotic control over the end effectors, the measured offsets may be stored in the tool memory and factored into the transforms generated by the Kernel. Hence, the storing of such calibration information can be used to overcome minor mechanical inconsistencies between tools of a single type. As described above, tool life and cumulative tool use information may also be stored on the tool memory and used by the processor to determine if the tool is still safe for use. Total tool life may be measured by clock time, by procedure, by the number of times the tool has been loaded onto a holder, and even by individual numbers of end effector actuations. Tool life data will preferably be stored in the memory of the tool using an irreversible writing process.

To perfect mechanical coupling between the driving elements of the holder (and the previously coupled rotatable bodies 134 of adapter 128), the supervisor initiates a "turn one way, turn the other way, and center" operation similar to that described above. To limit the range of motion of driven elements 118 and ensure pins 122 enter openings 140 of adapter 128, the holder may move axially to a proximal position so that the end effector is disposed within cannula 72 of manipulator 58 (see FIG. 2B). The axial positioning and rotation (turn, turn, and center) of the end effector are performed under steps ENGAGETOOL1-4, respectively.

The tool-type (and preferably tool-specific) data from tool memory 148 and/or the look-up table is sent to the middleman and/or Kernel software running on the coordinate transformation processor CTP for driving the appropriate coordinate transformations and generating the servo drive signals, as generally described above with reference to FIG. 10. The supervisor may then verify operation of the tool by manipulating the end effector per the calculated transforms, so as to complete the steps of path PD.

Figure 14A:
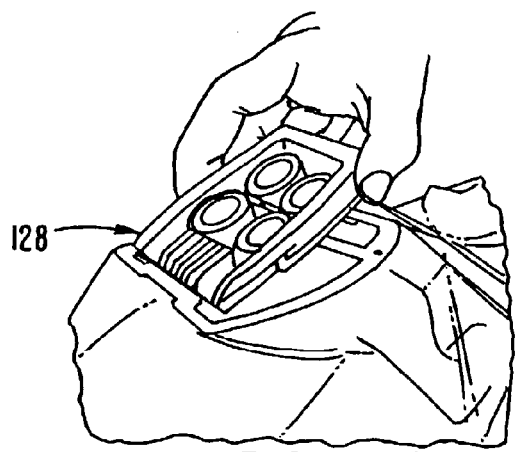
FIGS. 14A through C illustrate mounting of the adapter of FIGS. 7A through E to a manipulator arm, and of mounting the tool of FIG. 4 onto the adapter.
Figure 14B:
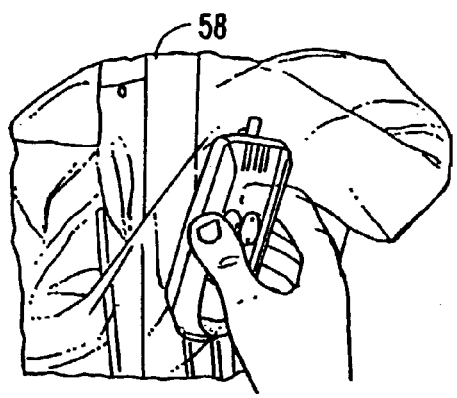
Figure 14C:
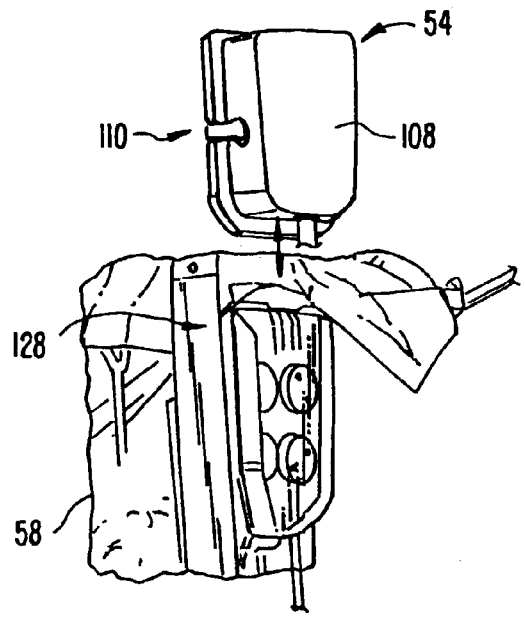

Methods for mounting adaptor 128 (together with a sterile drape) to the holder of manipulator 58 can be understood with reference to FIGS. 14A and B. Subsequent mounting of tool 54 to adapter 128 generally comprises inserting the surgical end effector distally through cannula 72 and sliding interface 110 of tool 54 into engagement with a mounted adapter, as illustrated in FIG. 14C. The tool can be removed and replaced by reversing the tool mounting procedure illustrated in FIG. 14C and mounting an alternative tool in its place.

Figure 15:
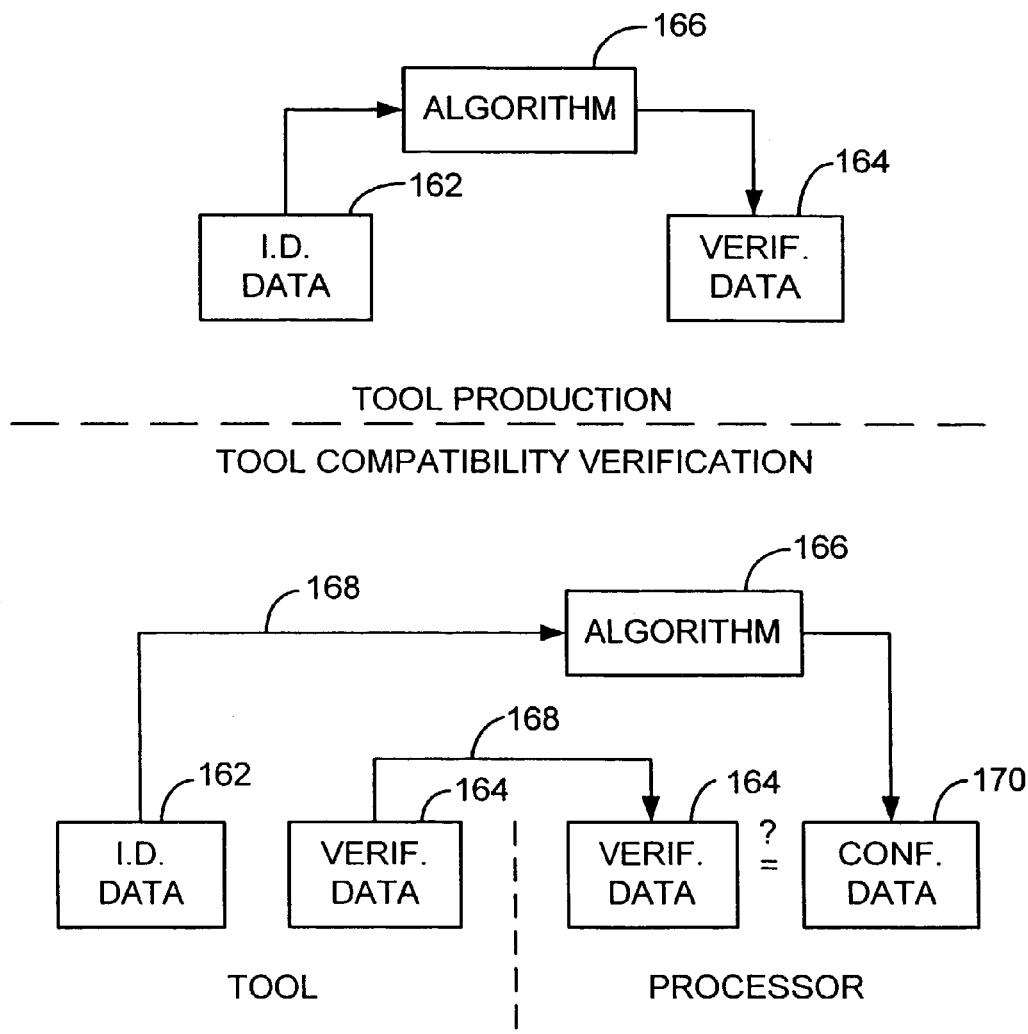
FIG. 15 schematically illustrates an exemplary tool compatibility verification algorithm according to the principles of the present invention.

Referring now to FIG. 15, an exemplary system and method for verifying compatibility of a tool with a robotic surgical system makes use of a unique identification data string that is irreversibly stored on an integrated circuit included in the circuitry of a tool or other component of the robotic surgical system. Advantageously, producers of such integrated circuits can include this unique identification data string on each integrated circuit such that no two integrated circuits include the same identification data. For example, Dallas DS 2505 may include a unique 64 bit identification data string which differs from the data strings of every other circuit of that part number.

The identification data string could be downloaded directly to the processor and compared with a table listing all identification data strings of circuits included in compatible tools. Such a table could then be updated each time additional tools were fabricated or outdated tools were retired.

To avoid continuously updating a compatible tool table, a verification data string 164 may be calculated from the unique identification data according to an algorithm 166. Algorithm 166 may be used as an encryption mechanism, typically using an arbitrary function which cannot easily be determined by sampling verification data and identification data from a few tools. Verification data string 164 may then be stored in a memory of the tool or other robotic component during tool production, typically using a non-volatile memory.

When the tool having identification data 162 and verification data 164 is coupled to the robotic surgical system, a signal 168 including these data strings may be transmitted to processor 152 as described above. By including a tangible media with method steps for performing algorithm 166 in a system accessible by processor 152, the processor can also perform the algorithm on the unique identification data so as to derive a conformation data string 170. This can be compared with the verification data, thereby confirming compatibility of the tool with the robotic system. Algorithm 166 may include any of a wide variety of known encryption algorithms, or may be developed specifically for use in the robotic surgical system of the present invention.

The descriptions given above regarding the exemplary devices, systems, and methods of the present invention are provided by way of an example, and for clarity of understanding. A wide variety of changes, modifications, and adaptations of these specific embodiments will be obvious to those of skill in the art. Hence, the invention is limited solely by the following claims.

What is claimed is:

1. A robotic surgical system, comprising:
   a drive assembly, said drive assembly operatively coupled to a control unit operable by inputs from an operator;
   a surgical instrument removably couplable to said drive assembly, said instrument having a proximal portion and a distal portion, said instrument including at least one distal end effector member, said proximal portion comprising a first plurality of movable bodies;
   said instrument comprising a plurality of joints, at least one of said joints being coupled to said end effector member, said joints being coupled to said first plurality of movable bodies by a plurality of drive members; and
   said drive assembly having a second plurality of movable bodies, said second plurality of movable bodies engageable with said first plurality of movable bodies such that the operator's inputs to the control unit cause the drive members to move, thereby producing a corresponding movement of at least one of said joints;
   wherein at least one of said first plurality of movable bodies is a rotatable body, at least one of said second plurality of movable bodies is a corresponding rotatable body, said at least one of said first plurality of movable bodies shares a single rotational axis with said corresponding one of said second plurality of movable bodies, rotation of said one of said second plurality of bodies about said single rotational axis generating a corresponding rotation of said one of said first plurality of bodies about said single rotational axis when said first and second plurality of bodies are operatively engaged.

2. The robotic surgical system of claim 1, wherein said instrument includes at least a shaft portion extending between said proximal and distal portions, at least one of said joints is disposed adjacent said distal portion, and said distal joint is coupled with at least one of said plurality of drive members which is housed within said shaft portion.

3. The robotic surgical system of claim 2, wherein one of said movable bodies causes rotation of the shaft portion.

4. The system of claim 1, further comprising a sterile coupling adaptor, said sterile adaptor being engageable with a surgical drape, and said adaptor including a plurality of intermediate movable bodies each transmissively couplable to corresponding ones of said first and second pluralities of movable bodies.

5. The robotic surgical system of claim 1, wherein said instrument includes at least two end effector members, each end effector member being movable independently of the other as a result of movement of at least two drive members, each drive member being engaged to one of said first plurality of movable bodies.

6. The robotic surgical system of claim 1, wherein said proximal and distal portions define an instrument axis extending generally from the proximal portion towards the distal portion, and one of the movable bodies engaged on the instrument causes rotation of the instrument about said instrument axis.

7. A robotic surgical system, comprising:
   a drive assembly, said drive assembly operatively coupled to a control unit operable by inputs from an operator;
   a surgical instrument removably couplable to said drive assembly, said instrument having a proximal portion and a distal portion, said instrument including at least one distal end effector member, said proximal portion comprising a first plurality of movable bodies;
   said instrument comprising a plurality of joints, at least one of said joints being coupled to said end effector member, said joints being coupled to said first plurality of movable bodies by a plurality of drive members; and
   said drive assembly having a second plurality of movable bodies, said second plurality of movable bodies engageable with said first plurality of movable bodies such that the operator's inputs to the control unit cause the drive members to move, thereby producing a corresponding movement of at least one of said joints;
   wherein at least one of said first plurality of movable bodies is a rotatable body, at least one of said second plurality of movable bodies is a corresponding rotatable body, and said at least one of said first plurality of movable bodies shares a single rotational axis with said corresponding one of said second plurality of movable bodies when said first and second plurality of bodies are operatively engaged, wherein at least one of said drive members comprises a flexible cable.

8. A robotic surgical system, comprising:
   a drive assembly comprising a plurality of links, joints and motors, said drive assembly operatively coupled to a control unit operable by inputs from an operator;
   a surgical instrument removably couplable to said drive assembly, said instrument having a proximal portion and a distal portion, said instrument including at least one distal end effector member, said proximal portion comprising a first plurality of movable bodies;
   said instrument comprising a plurality of joints, at least one of said joints being coupled to said end effector member, said joints being coupled to said first plurality of movable bodies by a plurality of drive members;
   said drive assembly having a second plurality of movable bodies coupled to said plurality of motors, said second plurality of movable bodies removably engageable with said first plurality of movable bodies such that said operator's inputs to the control unit cause the drive members to move, thereby producing a corresponding movement of at least one of said joints;

wherein at least one of said first plurality of movable bodies is a rotatable body, at least one of said second plurality of movable bodies is a corresponding rotatable body, and said at least one of said first plurality of movable bodies shares a single rotational axis with said corresponding one of said second plurality of movable bodies, rotation of said one of said second plurality of bodies about said single rotational axis generating a corresponding rotation of said one of said first plurality of bodies about said single rotational axis when said first and second plurality of movable bodies are operatively engaged.

9. The robotic surgical system of claim 8, wherein said instrument further comprises at least a second distal end effector member, each of said end effector members being movable independently of the other as a result of movement of at least two drive members, each drive member being engaged to one of said first plurality of movable bodies.

10. The robotic surgical system of claim 8, wherein said instrument includes at least a shaft portion extending between said proximal and distal portions, at least one of said joints is disposed adjacent said distal portion, and said distal joint is coupled with at least one of said plurality of drive members which is housed within said shaft portion.

11. The robotic surgical system of claim 10, wherein one of said movable bodies causes rotation of the shaft portion.

12. The system of claim 8, further comprising a sterile coupling adaptor, said sterile adaptor being engageable with a surgical drape, and said adaptor including a plurality of intermediate movable bodies each transmissively couplable to corresponding ones of said first and second pluralities of movable bodies.

13. The robotic surgical system of claim 8, wherein said instrument includes at least two end effector members, each end effector member being movable independently of the other as a result of movement of at least two drive members, each drive member being engaged to one of said first plurality of movable bodies.

14. The robotic surgical system of claim 8, wherein said proximal and distal portions define an instrument axis extending generally from the proximal portion towards the distal portion, and one of the movable bodies causes rotation of the instrument about said instrument axis.

15. A robotic surgical system, comprising:
a drive assembly comprising a plurality of links, joints and motors, said drive assembly operatively coupled to a control unit operable by inputs from an operator;
a surgical instrument removably couplable to said drive assembly, said instrument having a proximal portion and a distal portion, said instrument including at least one distal end effector member, said proximal portion comprising a first plurality of movable bodies;
said instrument comprising a plurality of joints, at least one of said joints being coupled to said end effector member, said joints being coupled to said first plurality of movable bodies by a plurality of drive members;
said drive assembly having a second plurality of movable bodies coupled to said plurality of motors, said second plurality of movable bodies removably engageable with said first plurality of movable bodies such that said operator's inputs to the control unit cause the drive members to move, thereby producing a corresponding movement of at least one of said joints;
wherein at least one of said first plurality of movable bodies is a rotatable body, at least one of said second plurality of movable bodies is a corresponding rotatable body, and said at least one of said first plurality of movable bodies shares a single rotational axis with said corresponding one of said second plurality of movable bodies when said first and second plurality of movable bodies are operatively engaged, wherein at least one of said instrument drive members is a flexible cable.

16. A robotic surgical system, comprising:
a drive assembly comprising a plurality of linkages and motors, said drive assembly operatively coupled to a control unit comprising a computer, said control unit operable by inputs from an operator;
surgical instrument removably couplable to said drive assembly, said instrument having a proximal portion having an interface and a distal portion, and the proximal portion comprising a first plurality of movable bodies;
said instrument including at least first and second distal end effector members, said first and second members coupled to corresponding first and second drive members;
said instrument further comprising a plurality of distal joints, at least one of said joints being coupled to said end effector members in such a manner that said end effector members are movable independently of each other as a result of movement of said drive members, each drive member being engaged to one of said first plurality of movable bodies;
said joints being coupled to said first plurality of movable bodies by a plurality of drive members;
said drive assembly having a second plurality of movable bodies coupled to said plurality of motors, said second plurality of movable bodies removably engageable with said first plurality of movable bodies such that said operator's inputs to the control unit cause the drive members to move, thereby producing a corresponding movement of at least one of said joints;
wherein at least one of said first plurality of movable bodies is a rotatable body, at least one of said second plurality of movable bodies is a corresponding rotatable body, and said at least one of said first plurality of movable bodies shares a single rotational axis with said corresponding one of said second plurality of movable bodies, rotation of said one of said second plurality of bodies about said single rotational axis generating a corresponding rotation of said one of said first plurality of bodies about said single rotational axis when said first and second plurality of movable bodies are operatively engaged.

17. The robotic surgical system of claim 16, wherein at least one of said first plurality of movable bodies includes an arcuate edge.

18. The robotic surgical system of claim 16, wherein each of said first plurality of movable bodies engages with one of said plurality of drive members.

19. The robotic surgical system of claim 16, wherein each of said first plurality of movable bodies includes a major surface, each of said first plurality of movable bodies being rotatable about an axis normal to its major surface.

20. The robotic surgical system of claim 16, wherein each of said first plurality of movable bodies includes an arcuate edge and a major surface, each of said first plurality of movable bodies being rotatable about an axis normal to its major surface.

21. The robotic surgical system of claim 16, wherein at least one of said first plurality of movable bodies is asymmetric relative to said axis.

22. The robotic surgical system of claim 16, wherein each of said first plurality of movable bodies of said instrument removably mechanically engages with one of said second plurality of movable bodies of said drive assembly.

23. The robotic surgical system of claim 16, wherein each of said first plurality of movable bodies of said instrument are removably mechanically engageable with one of said second plurality of movable bodies of said drive assembly substantially simultaneously.

24. The robotic surgical system of claim 16, wherein each of said first plurality of movable bodies of said instrument comprises a plurality of mechanical protrusions, each of said first plurality of movable bodies removably mechanically engageable with said second plurality of movable bodies of said drive assembly via said mechanical protrusions.

25. The robotic surgical system of claim 16, wherein each of said first plurality of movable bodies of said instrument comprises at least one mechanical protrusion, each of said first plurality of movable bodies removably mechanically engageable with said second plurality of movable bodies of said drive assembly via said mechanical protrusion, wherein each of said first plurality of movable bodies is mechanically asymmetric relative to a rotational axis of each of said first plurality of movable bodies.

26. The system of claim 16, wherein a sterile adaptor is interposed between said first plurality of movable bodies of said instrument and said second set of movable bodies of said drive assembly.

27. The robotic surgical system of claim 26, wherein said first set of movable bodies of said instrument engages said sterile adaptor and said sterile adaptor engages said second set of movable bodies of said drive assembly.

28. A robotic surgical system, comprising:
a drive assembly comprising a plurality of linkages and motors, said drive assembly operatively coupled to a control unit comprising a computer, said control unit operable by inputs from an operator;
a surgical instrument removably couplable to said drive assembly, said instrument having a proximal portion having an interface and a distal portion, and the proximal portion comprising a first plurality of movable bodies;
said instrument including at least first and second distal end effector members, said first and second members coupled to corresponding first and second drive members;
said instrument further comprising a plurality of distal joints, at least one of said joints being coupled to said end effector members in such a manner that said end effector members are movable independently of each other as a result of movement of said drive members, each drive member being engaged to one of said first plurality of movable bodies;
said joints being coupled to said first plurality of movable bodies by a plurality of drive members;
said drive assembly having a second plurality of movable bodies coupled to said plurality of motors, said second plurality of movable bodies removably engageable with said first plurality of movable bodies such that said operator's inputs to the control unit cause the drive members to move, thereby producing a corresponding movement of at least one of said joints;
wherein at least one of said first plurality of movable bodies is a rotatable body, at least one of said second plurality of movable bodies is a corresponding rotatable body, and said at least one of said first plurality of movable bodies shares a single rotational axis with said corresponding one of said second plurality of movable bodies when said first and second plurality of movable bodies are operatively engaged, wherein each of said first plurality of movable bodies is substantially similarly shaped.

29. A robotic surgical system, comprising:
a drive assembly comprising a plurality of linkages and motors, said drive assembly operatively coupled to a control unit comprising a computer, said control unit operable by inputs from an operator;
a surgical instrument removably couplable to said drive assembly, said instrument having a proximal portion having an interface and a distal portion, and the proximal portion comprising a first plurality of movable bodies;
said instrument including at least first and second distal end effector members, said first and second members coupled to corresponding first and second drive members;
said instrument further comprising a plurality of distal joints, at least one of said joints being coupled to said end effector members in such a manner that said end effector members are movable independently of each other as a result of movement of said drive members, each drive member being engaged to one of said first plurality of movable bodies;
said joints being coupled to said first plurality of movable bodies by a plurality of drive members;
said drive assembly having a second plurality of movable bodies coupled to said plurality of motors, said second plurality of movable bodies removably engageable with said first plurality of movable bodies such that said operator's inputs to the control unit cause the drive members to move, thereby producing a corresponding movement of at least one of said joints;
wherein at least one of said first plurality of movable bodies is a rotatable body, at least one of said second plurality of movable bodies is a corresponding rotatable body, and said at least one of said first plurality of movable bodies shares a single rotational axis with said corresponding one of said second plurality of movable bodies when said first and second plurality of movable bodies are operatively engaged, wherein each of said first plurality of movable bodies engages with one of said plurality of drive members, each of said drive members engaging with each of said movable bodies in a similar manner.

30. A robotic surgical system, comprising:
a drive assembly comprising a plurality of linkages and motors, said drive assembly operatively coupled to a control unit comprising a computer, said control unit operable by inputs from an operator;
a surgical instrument removably couplable to said drive assembly, said instrument having a proximal portion having an interface and a distal portion, and the proximal portion comprising a first plurality of movable bodies;
said instrument including at least first and second distal end effector members, said first and second members coupled to corresponding first and second drive members;
said instrument further comprising a plurality of distal joints, at least one of said joints being coupled to said end effector members in such a manner that said end effector members are movable independently of each other as a result of movement of said drive members, each drive member being engaged to one of said first plurality of movable bodies;
said joints being coupled to said first plurality of movable bodies by a plurality of drive members;
said drive assembly having a second plurality of movable bodies coupled to said plurality of motors, said second plurality of movable bodies removably engageable with said first plurality of movable bodies such that said operator's inputs to the control unit cause the drive members to move, thereby producing a corresponding movement of at least one of said joints;

wherein at least one of said first plurality of movable bodies is a rotatable body, at least one of said second plurality of movable bodies is a corresponding rotatable body, and said at least one of said first plurality of movable bodies shares a single rotational axis with said corresponding one of said second plurality of movable bodies when said first and second plurality of movable bodies are operatively engaged, wherein said instrument further comprises a proximal latch for releasing said surgical instrument from said drive assembly.

31. A robotic surgical system, comprising:

a drive assembly, said drive assembly operatively coupled to a control unit operable by inputs from an operator;

a surgical instrument having an elongate shaft with a proximal portion and a distal portion, said instrument removably couplable to said drive assembly, said proximal portion comprising a first plurality of movable bodies, said distal portion coupled to said first plurality of movable bodies by a plurality of drive members, and said distal portion movable in at least one degree of freedom;

said drive assembly having a second plurality of movable bodies, said second plurality of movable bodies engageable with said first plurality of movable bodies such that the operator's inputs to the control unit cause the drive members to move, thereby producing a corresponding movement of said distal portion; and wherein at least one of said first plurality of movable bodies is a rotatable body, at least one of said second plurality of movable bodies is a corresponding rotatable body, and said at least one of said first plurality of movable bodies shares a single rotational axis with said corresponding one of said second plurality of movable bodies of said one of said second plurality of bodies about said single rotational axis generating a corresponding rotation of said one of said first plurality of bodies about said single rotational axis when said first and second plurality of movable bodies are operatively engaged.

* * * * *